US009464117B2

(12) United States Patent
Wu et al.

(10) Patent No.: US 9,464,117 B2
(45) Date of Patent: Oct. 11, 2016

(54) HERBICIDE-RESISTANT PROTEINS, ENCODING GENES, AND USES THEREOF

(71) Applicants: Beijing Dabeinong Technology Group Co., Ltd., Haidian District, Beijing (CN); Beijing Dabeinong Technology Group Co., Ltd., Biotech Center, Haidian District, Beijing (CN); Beijing Green Agrosino Plant Protection Technology Co., Ltd., Haidian District, Beijing (CN)

(72) Inventors: Yechun Wu, Beijing (CN); Qing Tao, Beijing (CN); Derong Ding, Beijing (CN); Dengyuan Wang, Beijing (CN); Haili Liu, Beijing (CN); Xiaoqian Song, Beijing (CN); Tiantian Xing, Beijing (CN); Liguo Du, Beijing (CN); Songsong Shang, Beijing (CN); Xiaoming Bao, Beijing (CN)

(73) Assignees: BEIJING DABEINONG TECHNOLOGY GROUP CO., LTD, Beijing (CN); BEIJING DABEINONG TECHNOLOGY GROUP CO., LTD., BIOTECH CENTER, Beijing (CN); BEIJING GREEN AGROSINO PLANT PROTECTION TECHNOLOGY CO., LTD., Beijing (CN)

( * ) Notice: Subject to any disclaimer, the term of this patent is extended or adjusted under 35 U.S.C. 154(b) by 0 days.

(21) Appl. No.: 14/139,898

(22) Filed: Dec. 24, 2013

(65) Prior Publication Data
US 2014/0179534 A1 Jun. 26, 2014

(30) Foreign Application Priority Data

Dec. 25, 2012 (CN) .......................... 2012 1 0570647

(51) Int. Cl.
*C07K 14/00* (2006.01)
*C07K 14/415* (2006.01)

(52) U.S. Cl.
CPC .......... *C07K 14/001* (2013.01); *C07K 14/415* (2013.01)

(58) Field of Classification Search
None
See application file for complete search history.

(56) References Cited

U.S. PATENT DOCUMENTS 5,605,793 A 2/1997 Stemmer
8,916,752 B2 12/2014 Wright et al.
(Continued)

FOREIGN PATENT DOCUMENTS

WO 2005107437 A2 11/2005

OTHER PUBLICATIONS

Evertsz, E. M., et al. "Research Report Hybridization Cross-Reactivity within Homologous Gene Families on Glass cDNA Microarrays." Biotechniques 31.5 (2001.*

(Continued)

*Primary Examiner* — Amjad Abraham
*Assistant Examiner* — Weihua Fan
(74) *Attorney, Agent, or Firm* — Scully, Scott, Murphy & Presser, P.C.

(57) ABSTRACT

Some embodiments of the present invention can include herbicide-resistant proteins, coding genes, and uses thereof. Certain herbicide-resistant proteins can comprises: (a) a protein consisting of an amino acid sequence shown in SEQ ID NO: 2; or (b) a protein consisting of an amino acid sequence at least 90% identical to that set forth in SEQ ID NO: 2. Other herbicide-resistant proteins of this disclosure can be suitable for expression in plants, can have resistance to herbicides (e.g., to phenoxy auxinherbicides), or both.

12 Claims, 6 Drawing Sheets

(56) References Cited

U.S. PATENT DOCUMENTS

2003/0154507 A1* 8/2003 Oliver .............. C12N 15/8274
  800/278
2009/0093366 A1* 4/2009 Wright .............. C12N 9/0069
  504/142

OTHER PUBLICATIONS

Cunningham et al., "High-Resolution Epitope Mapping of hGH-Receptor Interactions by Alanine-Scanning Mutagenesis" Science (1989) vol. 244, pp. 1081-1085.
De Vos et al., "Human Growth Hormone and Extracellular Domain of Its Receptor: Crystal Structure of the Complex" Science (1992) vol. 255, pp. 306-312.
Neurath et al., The Protein, Third edition, vol. IV (1979) Academic Press, New York; Introduction and pp. 15-17.
Smith et al., "Human Interleukin 4 The Solution Structure of a Four-helix Bundle Protein" J. Mol. Biol. (1992) vol. 224, pp. 899-904.
Wlodaver et al., "Crystal structure of human recombinant interleukin-4 at 2.25 Angstrom resolution" FEBS Letters (1992) vol. 309, No. 1, pp. 59-64.
Hogan et al., "Distribution of the tfdA Gene in Soil Bacteria That Do Not Degrade 2,4-Dichlorophenoxyacetic Acid (2,4-D)" Microb. Ecol. (1997) vol. 34, pp. 90-96.
Genbank Accession No. AAP88277.1, 2 pages.
Schleinitz et al., "Localization and Characterization of Two Novel Genes Encoding Stereospecific Dioxygenases Catalyzing 2(2,4-Dichlorophenoxy)propionate Cleavage in Delftia acidovorans MC1" Applied and Environmental Microbiology (2004) vol. 70, No. 9, pp. 5357-5365.

\* cited by examiner

Water  1x 2,4-D  1xMCPA
*Arabidopsis* (Wild type)

Water  1x 2,4-D  1xMCPA
*Arabidopsis* (control sequence)

Water  1x 2,4-D  1xMCPA
24DT07 *Arabidopsis*

SEQUENCE LISTING

<160> NUMBER OF SEQ ID NOS: 19

<210> SEQ ID NO 1
<211> LENGTH: 882
<212> TYPE: DNA
<213> ORGANISM: Artificial Sequence
<220> FEATURE:
<223> OTHER INFORMATION: 24DT07 nucleotide sequence

<400> SEQUENCE: 1

```
atgtcgtccc tggaacttac cccgcttcac ccacttttcg ctgctgaggc aagaggaata    60
gatattaggc aaccgctgtc gccgtcggag gttaagcaga ttaacgccgc tatgaacaga   120
tacgcagtgc tggtttggag gggacagcca cttacggac agcaacagat cgacttcgcc   180
aaggcttttg gtccacttga tttggggctc aagaaagtct tcaaaaggcc tgaacgcttg   240
gaggatgaaa ggctcataga catttccaat gtggatgcag agggaaaggt tgcgaggcgc   300
gacagcccaa aaaacttgtc aaatttcgca aaccaactct ggcactctga ttcctctttt   360
cagaatcccc gcgcagcgta cagtatgctc catgcactgg tgcttccatc gtggggagga   420
aacacagagt tcgccgaact gagagccgct tatgacgctc ttcctgaaag aacgcggagt   480
gagattgaag gcttgagagc agagcactac gcgctccata ccaggattct cctgggagat   540
```

```
gaggcctata ctgatgacca aaagaaagcc attccacctg ctgtttggcc actggctcag    600
acgcacccag gtagcgggag aaagcttttg tttgtcggtg tgcatgcaag ggaaattatc    660
ggatggccag tcgcagaggg aaggatgttc ctttcagacc tcctggagca cgccacaaga    720
cgggaatttg tgtacacgca tgagtggcaa gttggggacc tggtcatgtg ggataacaga    780 tctaccctte accggggtag cgctatgac atcggggaga cgggaatt gaggcgcacc    840 actatagagg atgtgccaga agctactctc atggcagcgt aa                       882
```

```
<210> SEQ ID NO 2
<211> LENGTH: 293
<212> TYPE: PRT
<213> ORGANISM: Artificial Sequence
<220> FEATURE:
<223> OTHER INFORMATION: 24DT07 amino acid sequence

<400> SEQUENCE: 2
```

```
Met Ser Ser Leu Glu Leu Thr Pro Leu His Pro Leu Phe Ala Ala Glu
1               5                   10                  15

Ala Arg Gly Ile Asp Ile Arg Gln Pro Leu Ser Pro Ser Glu Val Lys
            20                  25                  30

Gln Ile Asn Ala Ala Met Asn Arg Tyr Ala Val Leu Val Trp Arg Gly
        35                  40                  45

Gln Pro Leu Thr Gly Gln Gln Gln Ile Asp Phe Ala Lys Ala Phe Gly
    50                  55                  60

Pro Leu Asp Leu Gly Leu Lys Lys Val Phe Lys Arg Pro Glu Arg Leu
65                  70                  75                  80

Glu Asp Glu Arg Leu Ile Asp Ile Ser Asn Val Asp Ala Glu Gly Lys
                85                  90                  95

Val Ala Arg Arg Asp Ser Pro Lys Asn Leu Ser Asn Phe Ala Asn Gln
            100                 105                 110

Leu Trp His Ser Asp Ser Ser Phe Gln Asn Pro Arg Ala Ala Tyr Ser
        115                 120                 125

Met Leu His Ala Leu Val Leu Pro Ser Trp Gly Gly Asn Thr Glu Phe
    130                 135                 140

Ala Glu Leu Arg Ala Ala Tyr Asp Ala Leu Pro Glu Arg Thr Arg Ser
145                 150                 155                 160

Glu Ile Glu Gly Leu Arg Ala Glu His Tyr Ala Leu His Thr Arg Ile
                165                 170                 175

Leu Leu Gly Asp Glu Ala Tyr Thr Asp Asp Gln Lys Lys Ala Ile Pro
            180                 185                 190

Pro Ala Val Trp Pro Leu Ala Gln Thr His Pro Gly Ser Gly Arg Lys
        195                 200                 205

Leu Leu Phe Val Gly Val His Ala Arg Glu Ile Ile Gly Trp Pro Val
    210                 215                 220

Ala Glu Gly Arg Met Phe Leu Ser Asp Leu Leu Glu His Ala Thr Arg
225                 230                 235                 240

Arg Glu Phe Val Tyr Thr His Glu Trp Gln Val Gly Asp Leu Val Met
                245                 250                 255

Trp Asp Asn Arg Ser Thr Leu His Arg Gly Arg Tyr Asp Ile Gly
            260                 265                 270

Glu Arg Arg Glu Leu Arg Thr Thr Ile Glu Asp Val Pro Glu Ala
        275                 280                 285

Thr Leu Met Ala Ala
    290
```

<210> SEQ ID NO 3
<211> LENGTH: 882
<212> TYPE: DNA
<213> ORGANISM: Artificial Sequence
<220> FEATURE:
<223> OTHER INFORMATION: 24DT07 substituted nucleotide sequence

<400> SEQUENCE: 3

| | | |
|---|---|---|
| atgtcgtccc tggaacttac cccgcttcac ccacttttcg ctgctgaggc aagaggaata | 60 |
| gatattaggc aaccgctgtc gccgtcggag gttaagcaga ttaacgccgc tatgaacaga | 120 |
| tacgcagtgc tggtttggag gggacagcca cttacaggac agcaacagat cgacttcgcc | 180 |
| aaggcttttg gtccacttga tttggggctc aagaaagtct tcaaaaggcc tgaacgcttg | 240 |
| gaggatgaaa ggctcataga catttccaat gtggatgcag agggaaaggt tgcgaggcgc | 300 |
| gacagcccaa aaaacttgtc aaatttcgca aaccaactct ggcactctga ttcctctttt | 360 |
| cagaatcccc gcgcagcgta cagtatgctc catgcactgg tgcttccatc gtggggagga | 420 |
| aacacagagt tcgccgaact gagagccgct tatgacgctc ttcctgaaag aacgcggagt | 480 |
| gagattgaag gcttgagagc agagcactac gcgctccata ccaggattct cctgggagat | 540 |
| gaggcctata ctgatgacca aaagaaagcc attccacctg ctgtttggcc actggctcag | 600 |
| acgcacccag gtagcgggag aaagcttttg tttgtcggtg tgcatgcaag ggaaattatc | 660 |
| ggatggccag tcgcagaggg aaggatgttc ctttcagacc tcctggagca cgccacacag | 720 |
| cgggaatttg tgtacacgca tgagtggcaa gttggggacc tggtcatgtg ggataacaga | 780 |
| tctaccttc accggggtag gcgctatgac atcggggaga gacgggaatt gaggcgcacc | 840 |
| actatagagg atgtgccaga agctactctc atggcagcgt aa | 882 |

<210> SEQ ID NO 4
<211> LENGTH: 873
<212> TYPE: DNA
<213> ORGANISM: Artificial Sequence
<220> FEATURE:
<223> OTHER INFORMATION: 24DT07 truncated nucleotide sequence

<400> SEQUENCE: 4

| | | |
|---|---|---|
| atgtcgtccc tggaacttac cccgcttcac ccacttttcg ctgctgaggc aagaggaata | 60 |
| gatattaggc aaccgctgtc gccgtcggag gttaagcaga ttaacgccgc tatgaacaga | 120 |
| tacgcagtgc tggtttggag gggacagcca cttacaggac agcaacagat cgacttcgcc | 180 |
| aaggcttttg gtccacttga tttggggctc aagaaagtct tcaaaaggcc tgaacgcttg | 240 |
| gaggatgaaa ggctcataga catttccaat gtggatgcag agggaaaggt tgcgaggcgc | 300 |
| gacagcccaa aaaacttgtc aaatttcgca aaccaactct ggcactctga ttcctctttt | 360 |
| cagaatcccc gcgcagcgta cagtatgctc catgcactgg tgcttccatc gtggggagga | 420 |
| aacacagagt tcgccgaact gagagccgct tatgacgctc ttcctgaaag aacgcggagt | 480 |
| gagattgaag gcttgagagc agagcactac gcgctccata ccaggattct cctgggagat | 540 |
| gaggcctata ctgatgacca aaagaaagcc attccacctg ctgtttggcc actggctcag | 600 |
| acgcacccag gtagcgggag aaagcttttg tttgtcggtg tgcatgcaag ggaaattatc | 660 |
| ggatggccag tcgcagaggg aaggatgttc ctttcagacc tcctggagca cgccacaaga | 720 |
| cgggaatttg tgtacacgca tgagtggcaa gttggggacc tggtcatgtg ggataacaga | 780 |
| tctaccttc accggggtag gcgctatgac atcggggaga gacgggaatt gaggcgcacc | 840 |
| actatagagg atgtgccaga agctactctc taa | 873 |

<210> SEQ ID NO 5
<211> LENGTH: 891
<212> TYPE: DNA
<213> ORGANISM: Artificial Sequence
<220> FEATURE:
<223> OTHER INFORMATION: 24DT07 added nucleotide sequence

<400> SEQUENCE: 5

| | | | | | |
|---|---|---|---|---|---|
| atgtcgtccc | tggaacttac | cccgcttcac | ccacttttcg | ctgctgaggc | aagaggaata | 60 |
| gatattaggc | aaccgctgtc | gccgtcggag | gttaagcaga | ttaacgccgc | tatgaacaga | 120 |
| tacgcagtgc | tggtttggag | gggacagcca | cttacaggac | agcaacagat | cgacttcgcc | 180 |
| aaggcttttg | gtccacttga | tttggggctc | aagaaagtct | tcaaaaggcc | tgaacgcttg | 240 |
| gaggatgaaa | ggctcataga | catttccaat | gtggatgcag | agggaaaggt | tgcgaggcgc | 300 |
| gacagcccaa | aaaacttgtc | aaatttcgca | aaccaactct | ggcactctga | ttcctctttt | 360 |
| cagaatcccc | gcgcagcgta | cagtatgctc | catgcactgg | tgcttccatc | gtggggagga | 420 |
| aacacagagt | tcgccgaact | gagagccgct | tatgacgctc | ttcctgaaag | aacgcggagt | 480 |
| gagattgaag | gcttgagagc | agagcactac | gcgctccata | ccaggattct | cctgggagat | 540 |
| gaggcctata | ctgatgacca | aaagaaagcc | attccacctg | ctgtttggcc | actggctcag | 600 |
| acgcacccag | gtagcgggag | aaagcttttg | tttgtcggtg | tgcatgcaag | ggaaattatc | 660 |
| ggatggccag | tcgcagaggg | aaggatgttc | ctttcagacc | tcctggagca | cgccacaaga | 720 |
| cgggaatttg | tgtacacgca | tgagtggcaa | gttggggacc | tggtcatgtg | ggataacaga | 780 |
| tctaccctttc | accggggtag | cgcgctatgac | atcggggaga | gacggaatt | gaggcgcacc | 840 |
| actatagagg | atgtgccaga | agctactctc | atggcagcgg | cattggtcta | a | 891 |

<210> SEQ ID NO 6
<211> LENGTH: 1322
<212> TYPE: DNA
<213> ORGANISM: Artificial Sequence
<220> FEATURE:
<223> OTHER INFORMATION: Arabidopsis Ubiquitin (ubiquitin) 10 gene
      promoter

<400> SEQUENCE: 6

| | | | | | |
|---|---|---|---|---|---|
| gtcgacctgc | aggtcaacgg | atcaggatat | tcttgtttaa | gatgttgaac | tctatggagg | 60 |
| tttgtatgaa | ctgatgatct | aggaccggat | aagttcccct | cttcatagcg | aacttattca | 120 |
| aagaatgttt | tgtgtatcat | tcttgttaca | ttgttattaa | tgaaaaaata | ttattggtca | 180 |
| ttggactgaa | cacgagtgtt | aaatatggac | caggccccaa | ataagatcca | ttgatatatg | 240 |
| aattaaataa | caagaataaa | tcgagtcacc | aaaccacttg | cctttttaa | cgagacttgt | 300 |
| tcaccaactt | gatacaaaag | tcattatcct | atgcaaatca | ataatcatac | aaaaatatcc | 360 |
| aataacacta | aaaaattaaa | agaaatggat | aatttcacaa | tatgttatac | gataaagaag | 420 |
| ttactttttcc | aagaaattca | ctgattttat | aagcccactt | gcattagata | aatggcaaaa | 480 |
| aaaaacaaaa | aggaaaagaa | ataaagcacg | aagaattcta | gaaaatacga | aatacgcttc | 540 |
| aatgcagtgg | gacccacggt | tcaattattg | ccaattttca | gctccaccgt | atatttaaaa | 600 |
| aataaaacga | taatgctaaa | aaaatataaa | tcgtaacgat | cgttaaatct | caacggctgg | 660 |
| atcttatgac | gaccgttaga | aattgtggtt | gtcgacgagt | cagtaataaa | cggcgtcaaa | 720 |
| gtggttgcag | ccggcacaca | cgagtcgtgt | ttatcaactc | aaagcacaaa | tacttttcct | 780 |
| caacctaaaa | ataaggcaat | tagccaaaaa | caacttgcg | tgtaaacaac | gctcaataca | 840 |
| cgtgtcattt | tattattagc | tattgcttca | ccgccttagc | tttctcgtga | cctagtcgtc | 900 |

```
ctcgtctttt cttcttcttc ttctataaaa caatacccaa agcttcttct tcacaattca      960
gatttcaatt tctcaaaatc ttaaaaactt tctctcaatt ctctctaccg tgatcaaggt     1020
aaatttctgt gttccttatt ctctcaaaat cttcgatttt gttttcgttc gatcccaatt     1080
tcgtatatgt tctttggttt agattctgtt aatcttagat cgaagacgat tttctgggtt     1140
tgatcgttag atatcatctt aattctcgat tagggtttca taaatatcat ccgatttgtt     1200
caaataattt gagttttgtc gaataattac tcttcgattt gtgatttcta tctagatctg     1260
gtgttagttt ctagtttgtg cgatcgaatt tgtcgattaa tctgagtttt tctgattaac     1320
ag                                                                    1322

<210> SEQ ID NO 7
<211> LENGTH: 253
<212> TYPE: DNA
<213> ORGANISM: Artificial Sequence
<220> FEATURE:
<223> OTHER INFORMATION: Terminator of Nopaline synthetase gene

<400> SEQUENCE: 7
gatcgttcaa acatttggca ataaagtttc ttaagattga atcctgttgc cggtcttgcg      60
atgattatca tataatttct gttgaattac gttaagcatg taataattaa catgtaatgc     120
atgacgttat ttatgagatg ggttttatg attagagtcc cgcaattata catttaatac      180
gcgatagaaa acaaaatata gcgcgcaaac taggataaat tatcgcgcgc ggtgtcatct     240
atgttactag atc                                                        253

<210> SEQ ID NO 8
<211> LENGTH: 530
<212> TYPE: DNA
<213> ORGANISM: Artificial Sequence
<220> FEATURE:
<223> OTHER INFORMATION: Cauliflower mosaic virus 35S promoter

<400> SEQUENCE: 8
ccatggagtc aaagattcaa atagaggacc taacagaact cgccgtaaag actggcgaac      60
agttcataca gagtctctta cgactcaatg acaagaagaa aatcttcgtc aacatggtgg     120
agcacgacac gcttgtctac tccaaaaata tcaaagatac agtctcagaa gaccaaaggg     180
caattgagac ttttcaacaa agggtaatat ccggaaacct cctcggattc cattgcccag     240
ctatctgtca ctttattgtg aagatagtgg aaaaggaagg tggctcctac aaatgccatc     300
attgcgataa aggaaaggcc atcgttgaag atgcctctgc cgacagtggt cccaaagatg     360
gacccccacc cacgaggagc atcgtggaaa aagaagacgt tccaaccacg tcttcaaagc     420
aagtggattg atgtgatatc tccactgacg taagggatga cgcacaatcc cactatcctt     480
cgcaagaccc ttcctctata taaggaagtt catttcattt ggagaggaca                530

<210> SEQ ID NO 9
<211> LENGTH: 552
<212> TYPE: DNA
<213> ORGANISM: Artificial Sequence
<220> FEATURE:
<223> OTHER INFORMATION: Glufosinate acetyl transferase gene

<400> SEQUENCE: 9
atgtctccgg agaggagacc agttgagatt aggccagcta cagcagctga tatggccgcg      60
gtttgtgata tcgttaacca ttacattgag acgtctacag tgaactttag gacagagcca     120
caaacaccac aagagtggat tgatgatcta gagaggttgc aagatagata cccttggttg     180
```

```
gttgctgagg ttgagggtgt tgtggctggt attgcttacg ctgggccctg aaggctagg     240 aacgcttacg attggacagt tgagagtact gtttacgtgt cacataggca tcaaaggttg     300
ggcctaggat ccacattgta cacacatttg cttaagtcta tggaggcgca aggttttaag    360
tctgtggttg ctgttatagg ccttccaaac gatccatctg ttaggttgca tgaggctttg    420
ggatacacag cccggggtac attgcgcgca gctggataca agcatggtgg atggcatgat    480
gttggttttt ggcaaaggga ttttgagttg ccagctcctc aaggccagt  taggccagtt    540 acccagatct ga                                                        552

<210> SEQ ID NO 10
<211> LENGTH: 195
<212> TYPE: DNA
<213> ORGANISM: Artificial Sequence
<220> FEATURE:
<223> OTHER INFORMATION: Cauliflower mosaic virus 35S terminator

<400> SEQUENCE: 10
ctgaaatcac cagtctctct ctacaaatct atctctctct ataataatgt gtgagtagtt     60
cccagataag ggaattaggg ttcttatagg gtttcgctca tgtgttgagc atataagaaa   120
cccttagtat gtatttgtat ttgtaaaata cttctatcaa taaaatttct aattcctaaa   180
accaaaatcc agtgg                                                     195

<210> SEQ ID NO 11
<211> LENGTH: 1848
<212> TYPE: DNA
<213> ORGANISM: Artificial Sequence
<220> FEATURE:
<223> OTHER INFORMATION: Control sequence

<400> SEQUENCE: 11
atggacaaca acccaaacat caacgaatgc attccataca actgcttgag taacccagaa     60
gttgaagtac ttggtggaga acgcattgaa accggttaca ctcccatcga catctccttg    120
tccttgacac agtttctgct cagcgagttc gtgccaggtg ctgggttcgt tctcggacta    180
gttgacatca tctggggtat cttttggtcca tctcaatggg atgcattcct ggtgcaaatt    240
gagcagttga tcaaccagag gatcgaagag ttcgccagga accaggccat ctctaggttg    300
gaaggattga gcaatctcta ccaaatctat gcagagagct tcagagagtg gaagccgat    360 cctactaacc cagctctccg cgaggaaatg cgtattcaat tcaacgacat gaacagcgcc    420
ttgaccacag ctatcccatt gttcgcagtc cagaactacc aagttcctct cttgtccgtg    480
tacgttcaag cagctaatct tcacctcagc gtgcttcgag acgttagcgt gtttgggcaa    540
aggtggggat tcgatgctgc aaccatcaat agccgttaca acgaccttac taggctgatt    600
ggaaactaca ccgaccacgc tgttcgttgg tacaacactg gcttggagcg tgtctggggt    660
cctgattcta gagattggat tagatacaac cagttcagga gagaattgac cctcacagtt    720
ttggacattg tgtctctctt cccgaactat gactccagaa cctaccctat ccgtacagtg    780
tcccaactta ccagagaaat ctatactaac ccagttcttg agaacttcga cggtagcttc    840
cgtggttctg cccaaggtat cgaaggctcc atcaggagcc acacttgat ggacatcttg    900 aacagcataa ctatctacac cgatgctcac agaggagagt attactggtc tggacaccag    960
atcatggcct ctccagttgg attcagcggg cccgagttta cctttcctct ctatggaact   1020
atgggaaacg ccgctccaca acaacgtatc gttgctcaac taggtcaggg tgtctacaga   1080
accttgtctt ccaccttgta cagaagaccc ttcaatatcg gtatcaacaa ccagcaactt   1140
```

```
tccgttcttg acggaacaga gttcgcctat ggaacctctt ctaacttgcc atccgctgtt    1200
tacagaaaga gcggaaccgt tgattccttg gacgaaatcc caccacagaa caacaatgtg    1260
ccacccaggc aaggattctc ccacaggttg agccacgtgt ccatgttccg ttccggattc    1320
agcaacagtt ccgtgagcat catcagagct cctatgttct catggattca tcgtagtgct    1380
gagttcaaca atatcattcc ttcctctcaa atcacccaaa tcccattgac caagtctact    1440
aaccttggat ctgaacttc tgtcgtgaaa ggaccaggct tcacaggagg tgatattctt    1500
agaagaactt ctcctggcca gattagcacc ctcagagtta acatcactgc accactttct    1560
caaagatatc gtgtcaggat tcgttacgca tctaccacta acttgcaatt ccacacctcc    1620
atcgacggaa ggcctatcaa tcagggtaac ttctccgcaa ccatgtcaag cggcagcaac    1680
ttgcaatccg gcagcttcag aaccgtcggt tcactactc ctttcaactt ctctaacgga    1740
tcaagcgttt tcacccttag cgctcatgtg ttcaattctg gcaatgaagt gtacattgac    1800
cgtattgagt ttgtgcctgc cgaagttacc ttcgaggctg agtactga                1848
```

<210> SEQ ID NO 12
<211> LENGTH: 1992
<212> TYPE: DNA
<213> ORGANISM: Artificial Sequence
<220> FEATURE:
<223> OTHER INFORMATION: Corn Ubiquitin (ubiquitin) 1 gene promoter

<400> SEQUENCE: 12

```
ctgcagtgca gcgtgacccg gtcgtgcccc tctctagaga taatgagcat tgcatgtcta     60
agttataaaa aattaccaca tattttttt gtcacacttg tttgaagtgc agtttatcta    120
tctttataca tatatttaaa ctttactcta cgaataatat aatctatagt actacaataa    180
tatcagtgtt ttagagaatc atataaatga acagttagac atggtctaaa ggacaattga    240
gtattttgac aacaggactc tacagtttta tcttttagt gtgcatgtgt tctcctttt    300 ttttgcaaat agcttcacct atataatact tcatccattt tattagtaca tccatttagg    360
gtttagggtt aatggttttt atagactaat ttttttagta catctatttt attctatttt    420
agcctctaaa ttaagaaaac taaaactcta ttttagtttt tttatttaat aatttagata    480
taaaatagaa taaaataaag tgactaaaaa ttaaacaaat accctttaag aaattaaaaa    540
aactaaggaa acattttct tgtttcgagt agataatgcc agcctgttaa acgccgtcga    600
cgagtctaac ggacaccaac cagcgaacca gcagcgtcgc gtcgggccaa gcgaagcaga    660
cggcacggca tctctgtcgc tgcctctgga ccctctcga gagttccgct ccaccgttgg    720
acttgctccg ctgtcggcat ccagaaattg cgtggcggag cggcagacgt gagccggcac    780
ggcaggcggc ctcctcctcc tctcacggca cggcagctac gggggattcc tttcccaccg    840
ctccttcgct ttcccttcct cgcccgccgt aataaataga cacccctcc acaccctctt    900 tccccaacct cgtgttgttc ggagcgcaca cacacacaac cagatctccc ccaaatccac    960
ccgtcggcac ctccgcttca aggtacgccg ctcgtcctcc cccccccccc ctctctacct   1020
tctctagatc ggcgttccgg tccatggtta gggcccggta gttctacttc tgttcatgtt   1080
tgtgttagat ccgtgtttgt gttagatccg tgctgctagc gttcgtacac ggatgcgacc   1140
tgtacgtcag acacgttctg attgctaact tgccagtgtt tctctttggg gaatcctggg   1200
atggctctag ccgttccgca gacgggatcg atttcatgat ttttttgtt tcgttgcata   1260 gggtttggtt tgccctttc ctttatttca atatatgccg tgcacttgtt tgtcgggtca   1320
tcttttcatg cttttttttg tcttggttgt gatgatgtgg tctggttggg cggtcgttct   1380
```

```
agatcggagt agaattctgt tcaaactac ctggtggatt tattaatttt ggatctgtat    1440
gtgtgtgcca tacatattca tagttacgaa ttgaagatga tggatggaaa tatcgatcta    1500
ggataggtat acatgttgat gcgggtttta ctgatgcata tacagagatg cttttgttc    1560 gcttggttgt gatgatgtgg tgtggttggg cggtcgttca ttcgttctag atcggagtag    1620
aatactgttt caaactacct ggtgtattta ttaattttgg aactgtatgt gtgtgtcata    1680
catcttcata gttacgagtt taagatggat ggaaatatcg atctaggata ggtatacatg    1740
ttgatgtggg ttttactgat gcatatacat gatggcatat gcagcatcta ttcatatgct    1800
ctaaccttga gtacctatct attataataa acaagtatgt tttataatta ttttgatctt    1860
gatatacttg gatgatggca tatgcagcag ctatatgtgg attttttag ccctgccttc    1920 atacgctatt tatttgcttg gtactgtttc ttttgtcgat gctcaccctg ttgtttggtg    1980
ttacttctgc ag                                                        1992

<210> SEQ ID NO 13
<211> LENGTH: 1176
<212> TYPE: DNA
<213> ORGANISM: Artificial Sequence
<220> FEATURE:
<223> OTHER INFORMATION: Phosphomannose-isomerase gene

<400> SEQUENCE: 13
atgcaaaaac tcattaactc agtgcaaaac tatgcctggg gcagcaaaac ggcgttgact      60
gaactttatg gtatggaaaa tccgtccagc cagccgatgg ccgagctgtg gatgggcgca    120
catccgaaaa gcagttcacg agtgcagaat gccgccggag atatcgtttc actgcgtgat    180
gtgattgaga gtgataaatc gactctgctc ggagaggccg ttgccaaacg ctttggcgaa    240
ctgcctttcc tgttcaaagt attatgcgca gcacagccac tctccattca ggttcatcca    300
aacaaacaca attctgaaat cggttttgcc aagaaaatg ccgcaggtat cccgatggat    360
gccgccgagc gtaactataa agatcctaac cacaagccgg agctggtttt tgcgctgacg    420
cctttccttg cgatgaacgc gtttcgtgaa ttttccgaga ttgtctccct actccagccg    480
gtcgcaggtg cacatccggc gattgctcac ttttttacaac agcctgatgc cgaacgttta    540
agcgaactgt tcgccagcct gttgaatatg cagggtgaag aaaaatcccg cgcgctggcg    600
atttaaaaat cggccctcga tagccagcag ggtgaaccgt ggcaaacgat tcgtttaatt    660
tctgaatttt accggaaga cagcggtctg ttctccccgc tattgctgaa tgtggtgaaa    720
ttgaaccctg gcgaagcgat gttcctgttc gctgaaacac cgcacgctta cctgcaaggc    780
gtggcgctgg aagtgatggc aaactccgat aacgtgctgc gtgcgggtct gacgcctaaa    840
tacattgata ttccggaact ggttgccaat gtgaaattcg aagccaaacc ggctaaccag    900
ttgttgaccc agccggtgaa acaaggtgca gaactggact tcccgattcc agtggatgat    960
tttgccttct cgctgcatga ccttagtgat aaagaaacca ccattagcca gcagagtgcc   1020
gccattttgt tctgcgtcga aggcgatgca acgttgtgga aaggttctca gcagttacag   1080
cttaaaccgg gtgaatcagc gtttattgcc gccaacgaat caccggtgac tgtcaaaggc   1140
cacggccgtt tagcgcgtgt ttacaacaag ctgtaa                             1176

<210> SEQ ID NO 14
<211> LENGTH: 23
<212> TYPE: DNA
<213> ORGANISM: Artificial Sequence
<220> FEATURE:
<223> OTHER INFORMATION: Primer 1
```

```
<400> SEQUENCE: 14
cgctatgaac agatacgcag tgc                                           23

<210> SEQ ID NO 15
<211> LENGTH: 20
<212> TYPE: DNA
<213> ORGANISM: Artificial Sequence
<220> FEATURE:
<223> OTHER INFORMATION: Primer 2

<400> SEQUENCE: 15
aagccttggc gaagtcgatc                                               20

<210> SEQ ID NO 16
<211> LENGTH: 27
<212> TYPE: DNA
<213> ORGANISM: Artificial Sequence
<220> FEATURE:
<223> OTHER INFORMATION: Probe 1

<400> SEQUENCE: 16
tgctgtcctg taagtggctg tcccctc                                       27

<210> SEQ ID NO 17
<211> LENGTH: 23
<212> TYPE: DNA
<213> ORGANISM: Artificial Sequence
<220> FEATURE:
<223> OTHER INFORMATION: Primer 3

<400> SEQUENCE: 17
tgcgtattca attcaacgac atg                                           23

<210> SEQ ID NO 18
<211> LENGTH: 23
<212> TYPE: DNA
<213> ORGANISM: Artificial Sequence
<220> FEATURE:
<223> OTHER INFORMATION: Primer 4

<400> SEQUENCE: 18
cttggtagtt ctggactgcg aac                                           23

<210> SEQ ID NO 19
<211> LENGTH: 24
<212> TYPE: DNA
<213> ORGANISM: Artificial Sequence
<220> FEATURE:
<223> OTHER INFORMATION: Probe2

<400> SEQUENCE: 19
cagcgccttg accacagcta tccc                                          24
```

HERBICIDE-RESISTANT PROTEINS, ENCODING GENES, AND USES THEREOF

CROSS-REFERENCE TO RELATED APPLICATION

This application claims priority under 35 U.S.C. §119(a)-(d) of Chinese Patent Application No. 201210570647.9 filed Dec. 25, 2012, entitled "Herbicide-resistant protein, encoding gene and use thereof" which is herein incorporated by reference in its entirety.

TECHNICAL FIELD

The present application relates to herbicide-resistant proteins, encoding genes, and uses thereof, especially a 2,4-D-resistant protein, encoding gene and use thereof.

BACKGROUND

Weeds can quickly run out of the valuable nutrients in the soil which are necessary for the growth of crops and other target plants. At present, there are many types of herbicides for weeds control, among which is a particularly popular herbicide, glyphosate. Glyphosate-resistant crops have been developed, such as corn, soybean, cotton, beet, wheat, and rice, and the like. Thus, it is possible to spray glyphosate in the fields planted with glyphosate-resistant crops to control weeds without significant damage to the crops.

Glyphosate has been widely used all over the world for more than 20 years, resulting in the overdependence on the technology of glyphosate and glyphosate-tolerant crops. In addition, high selection pressure has been forced to the naturally more glyphosate-tolerant plants among the wild weed species or the plants which have developed resistance to glyphosate activity. It has reported that a few weeds have developed resistance to glyphosate, including broad-leaved weeds and gramineous weeds, such as *Swiss ryegrass, Lolium multiflorum, Eleusine indica, Ambrosia artemisiifolia, Conyza canadensis, Conyza bonariensis* and *Plantago lanceolata*. In addition, the weeds which are not the agricultural problem before the widespread use of glyphosate-tolerant crops also gradually prevailed, and are difficult to be controlled with glyphosate-tolerant crops. These weeds mainly exist along with (but not only with) broad-leaved weeds which are difficult to be controlled, such as species from *Amaranthus, Chenopodium, Taraxacum and Commelinaceae*.

In the area of glyphosate-resistant weeds or the weed species which are difficult to be controlled, growers can make up the weakness of the glyphosate through tank-mixing or using other herbicide which can control the omissive weeds. In most cases, a popular and effective tank-mixing partner used to control broad-leaved weeds is 2,4-dichlorophenoxyacetic acid (2,4-D). 2,4-D has been used to control broad-spectrum broad-leaved weeds more than 65 years under agriculture and non-crop conditions, and is still one of the most widely used herbicides in the world. The limit for further use of 2,4-D is that its selectivity in dicotyledonous plants (such as soybeans or cotton) is very low. Therefore, 2,4-D is generally not used on (and generally not close to) sensitive dicotyledonous plants. In addition, the use of 2,4-D on gramineous crops is limited to a certain extent by the properties of the potential crop damage. The combination of 2,4-D and glyphosate has already been used to provide a stronger sterilization process before planting the no-till soybeans and cotton. However, due to the sensitivity of these dicotyledonous species to 2,4-D, these sterilization processes must be carried out 14 to 30 days before planting.

Same as MCPA, 2-methyl-4-chloropropionic acid and 2,4-D propionic acid, 2,4-D is also a phenoxy alkanoic acid herbicide. 2,4-D is used to selectively control broad-leaved weeds in many monocotyledonous crops such as corn, wheat and rice, without serious damage to the target crops. 2,4-D is a synthetic auxin derivative of which the function is to disorder the normal cytohormone homeostasis and to hinder the balance of controlled growth.

2,4-D shows different levels of selectivity on certain plants (for example, dicotyledonous plants are more sensitive than gramineous plants). Different 2,4-D metabolisms in different plants are one explanation for the different levels of selectivity. Plants usually metabolize 2,4-D slowly. Thus, different activities of targeted points are more likely to explain different responses to 2,4-D of plants. Plant metabolism of 2,4-D is usually achieved through two steps of metabolism, e.g., the conjugation with amino acids or glucose following the hydroxylation in general.

As time goes on, the microbial populations have gradually developed effective, alternative pathways to degrade this particular foreign substance, which result in the complete mineralization of 2,4-D. Continuous application of herbicides on microbes can be used to select the microorganisms which use herbicides as carbon sources so as to make a competitive advantage in the soil. For this reason, 2,4-D was currently formulated with a relatively short soil half-life period and without obvious legacy effect on the subsequent crops, which promotes the application of 2, 4-D herbicide.

*Ralstonia eutropha* is one organism of which the ability for degrading 2,4-D has been widely studied. The gene encoding the enzyme in the first enzymatic step of mineralization pathway is tfdA. TfdA catalyzes the conversion of 2,4-D acid into dichlorophenol (DCP) through α-oxoglutarate-dependent dioxygenase reaction. DCP hardly has herbicide activity compared with 2,4-D. TfdA is used to introduce 2,4-D resistance into dicotyledonous plants which are usually sensitive to 2,4-D (such as cotton and tobacco) in transgenic plants.

A number of tfdA type genes have been identified which encode proteins capable of degrading 2,4-D in the environment. Many homologs are similar with tfdA (amino acid identity>85%) and have similar enzyme activity with tfdA. However, a large number of homologs have significantly lower identity (25-50%) with tfdA while contain characteristic residues associated with α-oxoglutarate-dependent dioxygenase $Fe^{2+}$ dioxygenases. Therefore, the substrate specificities of these different dioxygenases are indefinite. A unique instance which has low homology (28% amino acid identity) with tfdA is rdpA from *Sphingobium herbicidovorans*. It has been shown that this enzyme catalyzes the first step in the mineralization of (R)-2,4-D propionic acid (and other (R)-phenoxy propionic acids) and 2,4-D (phenoxyacetic acid).

With the emergence of glyphosate-resistant weeds and the expanded application of 2,4-D herbicide, it is necessary to introduce 2,4-D resistance into the target plants sensitive to 2,4-D. At present, no reports have been found about the expression levels of herbicide-resistant protein 24DT07 in plants and their herbicide tolerance.

SUMMARY

Some purposes of the present application is to provide herbicide-resistant proteins, coding genes, and uses thereof.

The present application is intentioned to provide a new 24DT07 gene which has higher herbicide tolerance in plants.

In one aspect, the present application provides a herbicide-resistant protein, comprising:

(a) a protein consisting of an amino acid sequence shown in SEQ ID NO: 2; or (b) a protein with the activity of aryloxy alkanoate di-oxygenase which is derived from the amino acid sequence in (a) by replacing and/or deleting and/or adding one or several amino acids in the same; or (c) a protein consisting of an amino acid sequence at least 90% identical to that set forth in SEQ ID NO: 2.

In some embodiments, said herbicide-resistant protein is a protein consisting of an amino acid sequence at least 95% identical to that set forth in SEQ ID NO: 2.

In some embodiments, said herbicide-resistant protein is a protein consisting of an amino acid sequence at least 99% identical to that set forth in SEQ ID NO: 2.

In one aspect, the present application provides a herbicide-resistant gene, comprising:

(a) a nucleotide sequence encoding said herbicide-resistant protein; or (b) a nucleotide sequence capable of hybridizing with the nucleotide sequence as defined in (a) under stringent conditions and encoding a protein with the aryloxy alkanoate di-oxygenase activity; or (c) the nucleotide sequence set forth in SEQ ID NO: 1.

The stringent conditions might be as follows: hybridization in 6×SSC (sodium citrate), 0.5% SDS (sodium dodecyl sulfate) solution at 65° C. and followed by washing membrane one time using 2×SSC, 0.1% SDS and 1×SSC, 0.1% SDS, respectively.

In another aspect, the present application also provides an expression cassette, comprising said herbicide-resistant gene under the regulation of operably linked regulatory sequence.

In one aspect, the present application further provides a recombinant vector, comprising said herbicide-resistant gene or said expression cassette.

In another aspect, the present application further provides a transgenic host cell comprising said herbicide-resistant gene or the expression cassette, wherein said transgenic host cell comprises plant cells, animal cells, bacteria, yeast, baculovirus, nematodes, or algae. In some embodiments, the transgenic host might be selected from a group consisting of plant, animal, bacteria, yeast, baculovirus, nematodes, and algae.

In some embodiments, said transgenic host is a plant selected from the group consisting of soybean, cotton, corn, rice, wheat, beet and sugarcane.

In one aspect, the present application further provides a method for producing a herbicide-resistant protein, comprising steps of:

obtaining the transgenic host cells;

cultivating the transgenic host cells under the conditions allowing for the production of the herbicide-resistant protein; and recovering the herbicide-resistant protein.

In one aspect, the present application also provides a method for extending the target range of herbicides, comprising a step of co-expressing of the nucleotide encoding said herbicide-resistant protein or the expression cassette with at least a second nucleotide encoding a herbicide-resistant protein different from the herbicide-resistant protein as described above or said herbicide-resistant protein encoded by the expression cassette.

In some embodiments, said second nucleotide encodes glyphosate-resistant protein, glufosinate ammonium-resistant protein, 4-hydroxyphenylpyruvate dioxygenase, acetohydroxyacid synthase, cytochrome protein or protoporphyrinogen oxidase.

Alternatively, said second nucleotide is a dsRNA which inhibits important genes in target insect pest.

In yet another aspect, the present application provides a transgenic host cell co-expressing the nucleotide encoding said herbicide-resistant protein or the expression cassette with at least a second nucleotide encoding a herbicide-resistant protein different from the herbicide-resistant protein as described above or said herbicide-resistant protein encoded by the expression cassette.

In some embodiments, said second nucleotide encodes glyphosate-resistant protein, glufosinate ammonium-resistant protein, 4-hydroxyphenylpyruvate dioxygenase, acetohydroxyacid synthase, cytochrome protein or protoporphyrinogen oxidase.

Alternatively, said second nucleotide is a dsRNA which inhibits important genes in target insect pest.

In some embodiments of the present application, the herbicide-resistant protein 24DT07 is expressed in a transgenic plant accompanied by the expressions of one or more glyphosate-resistant proteins and/or glufosinate-ammonium-resistant proteins. Such a co-expression of more than one kind of herbicide-resistant protein in a same transgenic plant can be achieved by transfecting and expressing the genes of interest in plants through genetic engineering. In addition, herbicide-resistant protein 24DT07 can be expressed in one plant (Parent 1) through genetic engineering operations and glyphosate-resistant protein and/or glufosinate-ammonium-resistant protein can be expressed in a second plant (Parent 2) through genetic engineering operations. The progeny plants expressing all genes of Parent1 and Parent 2 can be obtained by crossing Parent1 and Parent 2.

RNA interference (RNAi) refers to a highly conserved and effective degradation phenomenon of specific homologous mRNA induced by double-stranded RNA (dsRNA) during evolution. Therefore, RNAi technology could be applied to specifically knock out or shut down the expression of a specific gene.

In yet another aspect, the present application also provides a method for selecting transformed plant cells, comprising the steps of transforming multiple plant cells with the herbicide-resistant gene or the expression cassette and cultivating said cells at a herbicide concentration which allows the growth of the transformed cells expressing the herbicide-resistant gene or the expression cassette while kills the un-transformed cells or inhibits the growth of the un-transformed cells, wherein the herbicide is a phenoxy auxin.

In one aspect, the present application also provides a method for controlling weeds, comprising a step of applying an effective amount of herbicides to the field planted with crops containing said herbicide-resistant gene, said expression cassette or said recombinant vector.

In some embodiments, the herbicide is a phenoxy auxin.

In another aspect, the present application also provides a method for protecting plants from the damage caused by herbicides, comprising the step of introducing said herbicide-resistant gene, said expression cassette or said recombinant vector into plants such that the obtained plants produce a certain quantity of herbicide-resistant protein sufficient to protect them from the damage caused by herbicides.

In some embodiments, the said herbicide is a phenoxy auxin or aryloxy phenoxy propionate and said plants are selected from the group consisting of soybean, cotton, corn, rice, wheat, beet and sugarcane.

In one aspect, the present application also provides a method for controlling glyphosate-resistant weeds in a field planted with glyphosate-tolerant plants, comprising a step of applying an effective amount of herbicides to the field planted with glyphosate-tolerant plants containing said herbicide-resistant gene, said expression cassette or said recombinant vector.

In some embodiments, said herbicide is a phenoxy auxin and said glyphosate-tolerant plant is monocotyledon or dicotyledon.

In another aspect, the present application also provides a method for conferring crops with resistance to 2,4-D herbicides, comprising the steps of introducing said herbicide-resistant gene, said expression cassette or said recombinant vector into plants.

In some embodiments, said plants are selected from the group consisting of soybean, cotton, corn, rice, wheat, beet and sugarcane.

In yet another aspect, the present application relates to a method for controlling weeds comprising a step of applying an effective amount of herbicides to the field planted with crops containing the herbicide-resistant gene of present application.

In some embodiments, the herbicide-resistant gene is produced from a transgenic host cell selected from the group consisting of plant cells, animal cells, bacteria, yeast, baculovirus, nematodes and algae.

In some embodiments, the plant is selected from the group consisting of soybean, cotton, corn, rice, wheat, beet and sugarcane.

In some embodiments, the nucleotide encoding the herbicide-resistant protein or the herbicide-resistant gene is co-expressed in the plant with at least a second nucleotide encoding a herbicide-resistant protein different from that of present application.

In some embodiments, said second nucleotide encodes glyphosate-resistant protein, glufosinate ammonium resistant protein, 4-hydroxyphenylpyruvate dioxygenase, acetolactate synthase, cytochromes protein or protoporphyrinogen oxidase.

In some embodiments, the herbicide is a phenoxy auxin.

The herbicide-resistant gene, said expression cassette or said recombinant vector is introduced into plants. The conventional methods used in present application to introduce foreign DNA into plant cells include but are not limited to Agrobacterium-mediated transfection, Particle Bombardment, direct intake of DNA into protoplast, electroporation or silicon-mediated DNA introduction.

DETAILED DESCRIPTION

Figure 1:
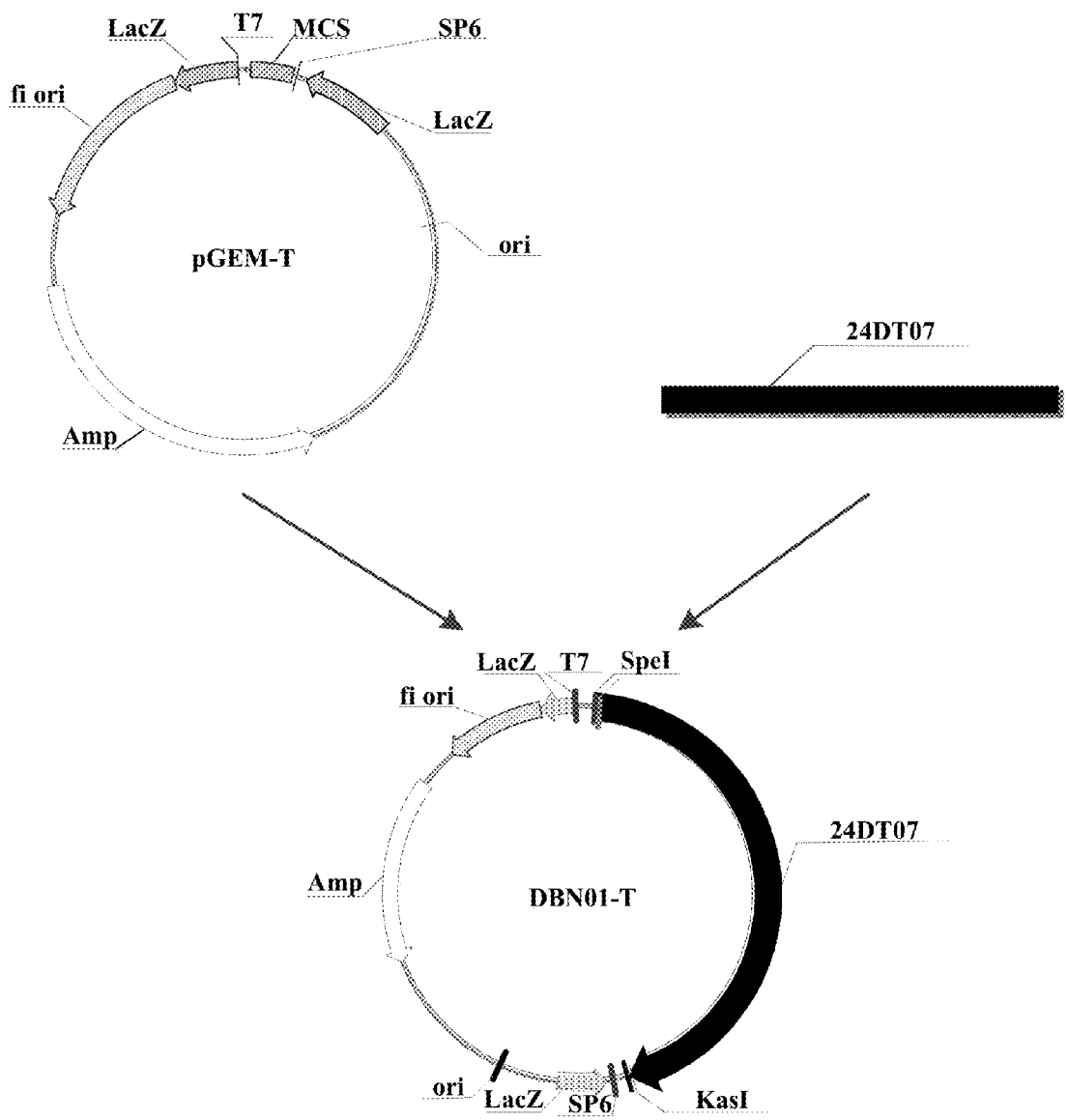
FIG. 1 shows the scheme to construct the recombinant cloning vector DBN01-T containing 24DT07 nucleotide sequence.

The 2,4-D resistance genes and subsequent resistance crops according to present application provide a good choice to control glyphosate-resistance (or high tolerance or succession) broad-leaved weed species in crops. 2,4-D is a broad-spectrum, relatively cheap and powerful broad-leaved herbicides. If stronger crop tolerance in both dicotyledons and monocots could be provided, good efficacies could be provided for growers. 2,4-D-tolerant transgenic dicotyledonons also have a higher flexibility in application time and administration amount. Another use of the 2,4-D herbicide-tolerance trait is that it could be used to prevent damages to normal sensitive crops such as 2,4-D drift, volatilization, transformation (or other remote movement phenomenon), misuse, destruction and the like. Various mixtures of different phenoxy auxins have been widely used to treat specific weed spectrum and environmental conditions in different areas. Using 24DT07 gene in plants can provide protections against broader-spectrum phenoxy auxin herbicide so as to improve the flexibility and controllable weed spectrum and provide protections to the full range of commercially available phenoxy auxin drift or other long distance phenoxy herbicides damages.

Phenoxy auxin herbicides are usually formulated as active acids, but some commercialized preparations are formulated as one of several corresponding ester preparations. Since general plant esterases in plants can convert these esters into active acids, they are also considered to be the substrates of 24DT07 enzyme in plants. Similarly, they can also be the organic or inorganic salts of the corresponding acids. When expressing chiral propionic acid, propionic acid salt or propionic ester herbicides, even if different CAS numbers may correspond to an optically pure compound. When denominating the herbicides, we still consider that racemic (R, S) or optically pure (R or S) enantiomer is a same herbicide. The possible dosage ranges can be those treated alone or combined with other herbicides in the applications in crops or non-crops.

It has been identified that the 24DT07 gene possesses the characteristics to allow the application of phenoxy auxin herbicide in plants after expressing the genetically engineered 24DT07 in plants, of which the inherent tolerance does not exist or is not enough to allow the application of these herbicides. In addition, 24DT07 gene can provide protection on phenoxy auxin herbicides when the natural tolerance is not enough to allow selectivity in plants. One, two or several phenoxy auxin herbicides can be continuously or tank-mixedly combined with it to treat plants only comprising 24DT07 gene. Dosage range of each phenoxy auxin herbicide used to control the broad-spectrum of dicotyledonous weeds ranges from 25 to 4000 g ae/ha, more generally from 100 to 2000 g ae/ha. Combination of these herbicides belonging to different chemical classes and having different action modes in a same field (continuously or tank-mixedly) can control most potential weeds which are intentioned to be controlled by the herbicides.

Glyphosate is widely used because it controls very broad spectrum of broad-leaved and gramineous weed species. However, the repeated use of glyphosate in the application of glyphosate-tolerant crops and non-crops has (and will continue to) selectively resulted in the succession of the weeds to species with more natural tolerance or glyphosate-resistant biotype. Most of the herbicide resistance management strategies recommend using effective amount of tank-mixed herbicide partners as a way to delay the appearance of resistant weeds. The herbicide partners provide the control of a same species but with different modes of action. The overlay of 24DT07 gene and glyphosate-tolerance trait (and/or other herbicide-tolerance traits) can provide the control of glyphosate-resistant weed species (broad-leaved weed species controlled by one or more phenoxy auxins) in glyphosate-tolerance crops by selectively applying glyphosate and phenoxy auxin (such as 2,4-D) on the same crops. Applications of these herbicides might be the individual use of single herbicide composition in a tank mixture containing two or more herbicides with different action models simultaneously or sequentially (e.g. before planting, before seedling emergence or after seedling emergence) (interval time ranged from 2 hours to 3 months). Alternatively, compositions of any number of herbicides representing every class of compound could be used at any time (from within 7 months after planting to the time of harvest (or, as to a single herbicide, it refers to preharvest interval in which the shortest one is selected)).

Flexibility is very important in the control of broad-leaved weeds, e.g., application time, dosage of a single herbicide and the ability to control stubborn or resistant weeds. The dosage of glyphosate which overlays with glyphosate-resistant gene/24DT07 gene can range from 250 to 2500 g ae/ha; the dose of (one or more) phenoxy auxin herbicides can range from 25 to 4000 g ae/ha. The optimum combination of the application time depends on the specific conditions, species and the environment.

Herbicide formulations (such as esters, acids or salt formulas or soluble concentrates, emulsified concentrates or soluble solutions) and additives of tank-mixture (such as adjuvant or compatilizer) can significantly affect the weed control of a given herbicide or a combination of one or more kinds of herbicides. Any chemical combinations of any of above herbicides are comprised in the scope of this application.

The benefits of the combination of two or more action modes in improving the controlled weed spectrum and/or natural species with more tolerance or resistance weed species can be extended to chemicals capable of producing other herbicide tolerances besides glyphosate-tolerance in crops through artificial means (transgenic or non-transgenic). In fact, the following resistance characteristics can be encoded alone or be multiply overlayed so as to provide the ability to effectively control or prevent weeds from succession to any category of the above-mentioned herbicide resistances: glyphosate resistance (such as resistant plant or bacteria, EPSPS, GOX, GAT), glufosinate-ammonium resistance (such as PAT, Bar), acetolactate synthase (ALS) inhibitory herbicide resistance (such as imidazolidinone, sulfonylurea, triazole pyrimidine, sulphonanilide, pyrimidine thiobenzoate and other chemical resistance genes such as AHAS, Csrl, SurA etc.), bromoxynil resistance (such as Bxn), resistance to inhibitor of HPPD (4-Hydroxyphenylpyruvate dioxygenase), resistance to inhibitor of phytoene desaturase (PDS), resistance to photosystem II inhibitory herbicide (such as psbA), resistance to photosystem I inhibitory herbicide, resistance to protoporphyrinogen oxidase IX (PPO) inhibitory herbicide (such as PPO-1), phenylurea herbicide resistance (such as CYP76B1), dicamba degrading enzyme etc.

As to other herbicides, some of other ALS inhibitors include triazolopyrimidine benzenesulfonamide (cloransulam-methyl, diclosulam, flumetsulam, metosulam and pyrimidino triazoles sulfonamide), pyrimidine thiobenzoate and flucarbazone. Some HPPD inhibitors include mesotrione, isoxaflutole and sulcotrione. Some PPO inhibitors include flumioxazin, butafenacil, carfentrazone, sulfentrazone and diphenyl oxide (such as acifluorfen, fomesafen, Lactofen and oxyfluorfen).

In addition, 24DT07 genes can be overlayed alone with one or more other input (such as insect resistance, fungus resistance or stress tolerance or output (such as the increased yield, improved oil mass, improved fiber quality) traits, or overlayed with one or more other input (such as insect resistance, fungus resistance or stress tolerance) or output (such as the increased yield, improved oil mass, improved fiber quality) traits after overlaying with other herbicide-resistant crop characteristics. Therefore, this application can provide the ability to flexibly and economically control any number of agronomy pests and a complete agronomy solution to improve crop quality.

24DT07 gene in this application can degrade 2,4-D, which is the basis of important herbicide-resistant crops and of the possibility of selection markers.

Almost all the herbicide combinations for broad-leaved weeds could be controlled by the transgenic expression of 24DT07 gene. 24DT07 gene as an excellent herbicide tolerant crop trait can be overlayed with, for example, other herbicide-tolerant crop characteristics, such as glyphosate resistance, glufosinate-ammonium resistance, ALS inhibitor (such as imidazolidinone, sulfonylurea and triazolopyrimidine benzenesulfonamides) resistance, bromoxynil resistance, HPPD inhibitor resistance, PPO inhibitor resistance and the like) and insect resistance traits (Cry1Ab, Cry1F, Vip3, other *bacillus thuringiensis* protein or insect-resistant protein derived from the non-bacillus). In addition, 24DT07 gene can be used as a selection marker to assist the selection of the primary transformant of plants genetically modified with another gene or genogroup.

Phenoxy alkanoate group can be used to introduce stable acid functional groups into herbicides. Acidic groups can import phloem activity by "acid capture" (the property required by herbicide effect) so as to be integrated into the new herbicides for activity purpose. There are many commercially available and experimental herbicides as substrates of 24DT07. Therefore, tolerances to other herbicides can be obtained by using present application.

The crop herbicide-tolerance trait of this application can be used in a new combination with other crop herbicide-tolerance traits (including but not limited to glyphosate tolerance). Because of the newly acquired resistance or inherent tolerance to herbicides (such as glyphosate), the combinations of these traits produce new methods to control weed species. Therefore, in addition to crop herbicide-tolerance traits, present application also includes new methods for controlling weeds by using herbicides, in which the said herbicide-tolerance is obtained through the enzyme produced by the transgenic crops.

The present application can be applied to a variety of plants, such as *arabidopsis*, tobacco, soybean, cotton, rice, corn and *brassica*. The present application can also be applied to a variety of other monocotyledonous (such as gramineous herbage or grassy carpet) and dicotyledonous crops (such as alfalfa, clover and tree species, etc.). Similarly, 2,4-D (or other 24DT07 substrates) can be applied more actively to gramineous crops with moderate tolerance, and the resulted tolerance of which traits are raised will provide growers the possibility to use these herbicides with more effective dosage and broader administration time without the risk of crop injury.

The genomes of plants, plant tissues or plant cells described in this application refer to any genetic materials in the plants, plant tissues or plant cells, and include the nucleus, plasmids and mitochondrial genomes.

The "resistance" described herein is heritable, and allows the plants to grow and reproduce under the case that effective treatment is applied to the given plants using common herbicide. Even if a certain damage of the plant caused by herbicides is obvious, the plant can still be considered "resistance". The term "tolerance" described herein is broader than the term "resistance" and includes "resistance" and the improved ability of particular plant resistant to the various degree of damages induced by the herbicides which result generally in the damages of the wild type plants with the same genotypes under the same herbicide dosage.

As described herein, polynucleotides and/or nucleotides form a complete "gene" and encode proteins or polypeptides in the host cells of interest. In some embodiments, the polynucleotides and/or nucleotides in the present application can be under the control of the regulatory sequences of the target host.

DNA exists typically as double strands. In such an arrangement, one strand is complementary with the other, and vice versa. When DNA is replicated in plants, other complementary strands of DNA are also generated. Therefore, the polynucleotides exemplified in the sequence listing and complementary strands thereof are comprised in this application. The "coding strand" generally used in the art refers to a strand binding with an antisense strand. To express a protein in vivo, one strand of the DNA is typically transcribed into a complementary strand of a mRNA, which serves as the template of protein expression. In fact, a mRNA is transcribed from the "antisense" strand of DNA. "Sense strand" or "coding strand" contains a series of codons (codon is a triplet of nucleotides that codes for a specific amino acid), which might be read as open reading frames (ORF) to generate target proteins or peptides. RNA and PNA (peptide nucleic acid) which are functionally equivalent with the exemplified DNA were also contemplated in this application.

Nucleic acid molecule or fragments thereof were hybridized with the herbicide-resistant gene under stringency condition in this application. Any regular methods of nucleic acid hybridization or amplification can be used to identify the existence of the herbicide-resistant gene in present application. Nucleic acid molecules or fragments thereof are capable of specifically hybridizing with other nucleic acid molecules under certain conditions. In present application, if two nucleic acid molecules can form an antiparallel nucleic acid structure with double strands, it can be determined that these two molecules can hybridize with each other specifically. If two nucleic acid molecules are completely complementary, one of two molecules is called as the "complement" of the other one. In this application, when every nucleotide of a nucleic acid molecule is complementary with the corresponding nucleotide of another nucleic acid molecule, it is identified the two molecules are "completely complementary". If two nucleic acid molecules can hybridize with each other so that they can anneal to and bind to each other with enough stability under at least normal "low-stringency" conditions, these two nucleic acids are identified as "minimum complementary". Similarly, if two nucleic acid molecules can hybridize with each other so that they can anneal to and bind to each other with enough stability under normal "high-stringency" conditions, it is identified that these two nucleic acids are "complementary". Deviation from "completely complementary" can be allowed, as long as the deviation does not completely prevent the two molecules to form a double-strand structure. A nucleic acid molecule which can be taken as a primer or a probe must have sufficiently complementary sequences to form a stable double-strand structure in the specific solvent at a specific salt concentration.

In this application, basically homologous sequence refers to a nucleic acid molecule, which can specifically hybridize with the complementary strand of another matched nucleic acid molecule under "high-stringency" condition. The stringency conditions for DNA hybridization can be any suitable conditions, such as treatment with 6.0× sodium chloride/sodium citrate (SSC) solution at about 45° C. and washing with 20.0×SSC at 50° C. For example, the salt concentration in the washing step is selected from 20.0×SSC and 50° C. for the "low-stringency" conditions and 0.2×SSC and 50° C. for the "high-stringency" conditions. In addition, the temperature in the washing step ranges from 22° C. for the "low-stringency" conditions to 65° C. for the "high-stringency" conditions. Both temperature and the salt concentration can vary together or only one of these two variables varies. In some instances, the stringency condition used in this application might be as below. SEQ ID NO:1 is specifically hybridized in 6.0×SSC and 0.5% SDS solution at 65° C. Then the membrane was washed one time in 2×SSC and 0.1% SDS solution and 1×SSC and 0.1% SDS solution, respectively.

Therefore, the herbicide-resistant sequences which can hybridize with SEQ ID NO: 1 under stringency conditions were comprised in this application. These sequences were at least about 40%-50% homologous or about 60%, 65% or 70% homologous, even at least 75%, 80%, 85%, 90%, 91%, 92%, 93%, 94%, 95%, 96%, 97%, 98%, 99% or higher homologous to the sequences of present application.

The present application provides functional proteins. "Functional activity" (or "activity") as described herein means the activity of proteins/enzymes (alone or combined with other protein) in this application to degrade herbicide or reduce the herbicide activity. The plants which produce the proteins of this application can, in some instances, produce such an effective amount of proteins that, when treating plants with herbicides, the protein expression level is enough to provide the plants with complete or partial resistance or tolerance to herbicides (general dosage if there are no specific instructions). Herbicides are usually applied at the dosage capable of killing the target plants, normal dosage and concentration applied in the field. In some instances, plant cells and plants of this application are protected from the growth inhibition or damage caused by herbicide treatment. The transformed plants and plant cells of the present application can, in some instances, have resistance or tolerance to 2,4-D herbicides, which means that the transformed plants and plant cells can survive in the condition with effective amount of 2,4-D herbicides.

Genes and proteins described in the present application include not only the specifically exemplified sequences, but also parts and/or fragments (including deletion(s) in and/or at the end of the full-length protein), variants, mutants, substitutes (proteins containing substituted amino acid(s)), chimeras and fusion proteins retaining the herbicide-resistant activity thereof. The said "variants" or "variation" refers to the nucleotide sequences encoding the same one protein or encoding an equivalent protein having herbicide-resistant activity. The said "equivalent protein" refers to the proteins that have the same or the substantially same bioactivity of herbicide-resistant activity as that of the claimed proteins.

The "fragment" or "truncation" of the DNA or protein sequences as described in this application refers to a part or an artificially modified form thereof (e.g., sequences suitable for plant expression) of the original DNA or protein sequences (nucleotides or amino acids) involved in present application. The sequence length of said sequence is variable, but it is long enough to ensure that the (encoded) protein is herbicide-resistant protein. In some cases (especially expression in plants), it is advantageous to use a truncated gene which encodes a truncated protein. The truncated gene can, in some instances. encode 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the whole protein.

Due to redundancy of the genetic codons, a variety of different DNA sequences can encode one same amino acid sequence. These different DNA sequences are comprised in this application. The said "substantially same" sequence refers to a sequence in which certain amino acids are substituted, deleted, added or inserted, but herbicide-resistant activity thereof is not substantially affected, and also includes the fragments remaining the herbicide-resistant activity.

Substitution, deletion or addition of some amino acids in amino acid sequences can, in some instances, be accomplished in this application by any suitable technique. Sometimes, such an amino acid change includes: minor characteristics change, e.g., substitution of reserved amino acids which do not significantly influence the folding and/or activity of the protein; short deletion, usually a deletion of about 1-30 amino acids; short elongation of amino or carboxyl terminal, such as a methionine residue elongation at amino terminal; short connecting peptide, such as about 20-25 residues in length.

The examples of conservative substitution are the substitutions happening in the following amino acids groups: basic amino acids (such as arginine, lysine and histidine), acidic amino acids (such as glutamic acid and aspartic acid), polar amino acids (e.g., glutamine and asparagine), hydrophobic amino acids (such as leucine, isoleucine, and valine), aromatic amino acids (e.g., phenylalanine, tryptophan and tyrosine), and small molecular amino acids (such as glycine, alanine, serine and threonine and methionine). Some amino acid substitutions generally not changing specific activity have been described in, for example, *Protein* edited by N. Neurath and R. L. Hill, published by Academic Press, New York in 1979. The most common substitutions are Ala/Ser, Val/Ile, Asp/Glu, Thu/Ser, Ala/Thr, Ser/Asn, Ala/Val, Ser/Gly, Tyr/Phe, Ala/Pro, Lys/Arg, Asp/Asn, Leu/Ile, Leu/Val, Ala/Glu and Asp/Gly, and reverse substitutions thereof.

Such a substitution may happen outside of the regions which are important to the molecular function and still cause the production of active polypeptides. For the polypeptide of the present application, the amino acid residues which are required for their activity and chosen as the unsubstituted residues can be identified according to the known methods of the art, such as site-directed mutagenesis or alanine-scanning mutagenesis (see, e.g. Cunningham and Wells, 1989, Science 244:1081-1085). The latter technique is carried out by introducing mutations in every positively charged residue in the molecule and detecting the herbicide-resistant activity of the obtained mutation molecules, so as to identify the amino acid residues which are important to the activity of the molecules. Enzyme-substrates interaction sites can also be determined by analyzing its three-dimensional structure, which can be determined through some techniques such as nuclear magnetic resonance (NMR) analysis, crystallography, or photoaffinity labeling (see, for example, de Vos et al., 1992, Science 255:306-312; Smith, et al., 1992, J. Mol. Biol 224:899-904; Wlodaver, et al., 1992, FEBS Letters 309:59-64).

Therefore, amino acid sequences which have certain homology with the amino acid sequences set forth in SEQ ID No. 2 are also comprised in this application. The sequence similarity/homology between these sequences and the sequences described in the present application can be more than 60%, more than 75%, more than 80%, more than 90% or more than 95%. Some of the polynucleotides and proteins in the present application can also be defined according to more specific ranges of the homology and/or similarity. For example, they have a homology and/or similarity of 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% with the sequences described in this application.

Regulatory sequences described in this application include but are not limited to a promoter, transit peptide, terminator, enhancer, leading sequence, introns and other regulatory sequences that can be operably linked to the said 24DT07 gene.

The said promoter is a promoter expressible in plants, wherein said "a promoter expressible in plants" refers to a promoter which ensures that the coding sequences bound with the promoter can be expressed in plant cells. The promoter expressible in plants can be a constitutive promoter.

The examples of promoters capable of directing the constitutive expression in plants include but are not limited to 35S promoter derived from Cauliflower mosaic virus, ubi promoter, promoter of GOS2 gene derived from rice and the like. Alternatively, the promoter expressible in plants can be a tissue-specific promoter, which means that the expression level directed by this promoter in some plant tissues such as in chlorenchyma, is higher than that in other tissues of the plant (can be measured through the conventional RNA test), such as the PEP carboxylase promoter. Alternatively, the promoter expressible in plants can be wound-inducible promoters as well. Wound-inducible promoters or promoters that direct wound-inducible expression manners refer to the promoters by which the expression level of the coding sequences can be increased remarkably compared with those under the normal growth conditions when the plants are subjected to mechanical wound or wound caused by the gnaw of insects. The examples of wound-inducible promoters include but are not limited to the promoters of genes of protease inhibitor of potatoes and tomatoes (pin I and pin II) and the promoters of maize protease inhibitor gene (MPI).

The said transit peptide (also called paracrine signal sequence or leader sequence) directs the transgenosis products into specific organelles or cellular compartments. For the receptor protein, the said transit peptide can be heterogeneous. For example, sequences encoding chloroplast transit peptide are used to lead to chloroplast; or 'KDEL' reserved sequence is used to lead to the endoplasmic reticulum or CTPP of the barley lectin gene is used to lead to the vacuole.

The said leader sequences include but are not limited to small RNA virus leader sequences, such as EMCV leader sequence (encephalomyocarditis virus 5' non coding region); Potato virus Y leader sequences, such as MDMV (Maize dwarf mosaic virus) leader sequence; human immunoglobulin heavy chain binding protein (BiP); untranslated leader sequence of the coat protein mRNA of Alfalfa Mosaic virus (AMV RNA4); Tobacco Mosaic virus (TMV) leader sequence.

The said enhancer includes but is not limited to Cauliflower Mosaic virus (CaMV) enhancer, Figwort Mosaic virus (FMV) enhancer, Carnations Etched Ring virus (CERV) enhancer, Cassava Vein Mosaic virus (CsVMV) enhancer, Mirabilis Mosaic virus (MMV) enhancer, Cestrum yellow leaf curling virus (CmYLCV) enhancer, Cotton leaf curl Multan virus (CLCuMV), Commelina yellow mottle virus (CoYMV) and peanut chlorotic streak mosaic virus (PCLSV) enhancer.

For the application of monocotyledon, the said introns include but are limited to maize hsp70 introns, maize ubiquitin introns, Adh intron 1, sucrose synthase introns or rice Act1 introns. For the application of dicotyledonous plants, the said introns include but are not limited to CAT-1 introns, pKANNIBAL introns, PIV2 introns and "super ubiquitin" introns.

The said terminators can be the proper polyadenylation signal sequences playing a role in plants. They include but are not limited to polyadenylation signal sequence derived from *Agrobacterium tumefaciens* nopaline synthetase (NOS) gene, polyadenylation signal sequence derived from protease inhibitor II (pin II) gene, polyadenylation signal sequence derived from peas ssRUBISCO E9 gene and polyadenylation signal sequence derived from α-tubulin gene.

The term "operably linked" described in this application refers to the linking of nucleic acid sequences, which provides the sequences the required function of the linked sequences. The term "operably linked" described in this application can be the linkage of the promoter with the sequences of interest, which makes the transcription of these sequences under the control and regulation of the promoter. When the sequence of interest encodes a protein and the expression of this protein is required, the term "operably linked" indicates that the linking of the promoter and said sequence makes the obtained transcript to be effectively translated. If the linking of the promoter and the coding sequence results in transcription fusion and the expression of the encoding protein are required, such a linking is generated to make sure that the first translation initiation codon of the obtained transcript is the initiation codon of the coding sequence. Alternatively, if the linking of the promoter and the coding sequence results in translation fusion and the expression of the encoding protein is required, such a linking is generated to make sure that the first translation initiation codon of the 5' untranslated sequence is linked with the promoter, and such a linking way makes the relationship between the obtained translation products and the open reading frame encoding the protein of interest meet the reading frame. Nucleic acid sequences that can be "operably linked" include but are not limited to sequences providing the function of gene expression (e.g., gene expression elements, such as a promoter, 5' untranslated region, introns, protein-coding region, 3' untranslated region, polyadenylation sites or transcription terminators); sequences providing the function of DNA transfer and/or integration (e.g., T-DNA boundary sequences, recognition sites of site-specific recombinant enzyme, integrase recognition sites); sequences providing selectable function (e.g., antibiotic resistance markers, biosynthetic genes); sequences providing the function of scoring markers; sequences assistant with the operation of sequences in vitro or in vivo (polylinker sequences, site-specific recombinant sequences) and sequences providing replication function (e.g., origins of replication of bacteria, autonomously replicating sequences, centromeric sequences).

This application can confer new herbicide resistant trait(s) to the plants while adverse effects on phenotypes including yield are not observed. The plants of present application can tolerate against 2×, 3×, 4× or 5× general application level of at least one subjected herbicide. The improvement of these resistance levels is in the scope of present application. For example, it is possible to foreseeably optimize and further develop many kinds of known technologies so as to increase the expression of a given gene.

In present application, said herbicide-resistant protein is 24DT07 amino acid sequence as shown in SEQ ID NO: 2 of the sequence listing. Said herbicide-resistant gene is 24DT07 nucleotide sequence as shown in SEQ ID NO: 1 of the sequence listing. In order to be applied to plants, said herbicide-resistant gene also contains, besides coding region of the protein encoded by 24DT07 nucleotide sequence, other elements, such as encoding regions which encode transit peptides, the coding regions which encode selective marker proteins or the proteins which confer resistance to insect.

The herbicide-resistant protein 24DT07 as describe herein is tolerant to most phenoxy auxin herbicides. The genomes of the plants in present application contain exogenous DNAs which contain 24DT07 nucleotide sequence. The plants are protected from the threat of herbicides by expressing an effective amount of this protein. "Effective amount" refers to the amount which causes no damage or causes slight damage to the plant; in some instances, the plants are morphologically normal or almost morphologically normal, and could be cultivated under the common means for the consumption and/or generation of products.

The expression level of herbicide-resistance crystal proteins (ICP) in the plant materials can be determined using various methods described in this field, such as the method of quantifying mRNA encoding the herbicide-resistant protein in the tissue through using specific primers, or the method of quantifying the herbicide-resistant protein directly and specifically.

Some embodiments of the present application provide herbicide-resistant proteins, coding genes, and uses thereof that can have one or more of following advantages:

1. Strong herbicide-resistance activity. Herbicide-resistant protein 24DT07 can be resistant to herbicides, such as phenoxy auxin herbicides, particularly 2,4-D.

2. Broad herbicide-resistance spectrum. The herbicide-resistant protein 24DT07 can show resistance to a variety of plant phenoxy auxin herbicides, therefore it has broad application prospect on the plants.

The technical solutions of this application will be further described through the appended figures and examples as following.

EXAMPLES

The technical solutions of herbicide-resistant proteins, coding genes, and uses thereof in present application will be further illustrated through the following examples.

Example 1

The Obtaining and Synthesis of 24DT07 Gene Sequence

1. Obtaining of 24DT07 Gene Sequence

Amino acid sequence of 24DT07 herbicide-resistant protein (293 amino acids) was shown as SEQ ID NO: 2 in the sequence listing; the nucleotide sequence (882 nucleotides) encoding the corresponding amino acid sequence of 24DT07 herbicide-resistant protein (293 amino acids) was shown as SEQ ID NO: 1 in the sequence listing.

2. Synthesis of the Nucleotide Sequence as Described Above

The 24DT07 nucleotide sequence (shown as SEQ ID NO: 1 in the sequence listing) was synthesized by GenScript CO., LTD, Nanjing, P.R. China. The synthesized 24DT07 nucleotide sequence (SEQ ID NO: 1) was linked with a SpeI restriction site at the 5' end and a KasI restriction site at the 3' end.

At the same time, the substituted 24DT07 nucleotide sequence (shown as SEQ ID NO: 3 in the sequence listing) was also synthesized, in which the Arg$^{240}$ was substituted with Gln. The synthesized, substituted 24DT07 nucleotide sequence (SEQ ID NO: 3) was linked with a SpeI restriction site at the 5' end and a KasI restriction site at the 3' end.

At the same time, the truncated 24DT07 nucleotide sequence (shown as SEQ ID NO: 4 in the sequence listing) was also synthesized, which is composed of the amino acids from 1 to 290 of 24DT07 amino acid sequence. The synthesized, truncated 24DT07 nucleotide sequence (SEQ ID NO: 4) was linked with a SpeI restriction site at the 5' end and a KasI restriction site at the 3' end.

At the same time, the added 24DT07 nucleotide sequence (shown as SEQ ID NO: 5 in the sequence listing) was also synthesized, in which three amino acids Ala, Leu and Val were added after the 293th amino acid of 24DT07 amino acid sequence. The synthesized, added 24DT07 nucleotide sequence (SEQ ID NO: 5) was linked with a SpeI restriction site at the 5' end and a KasI restriction site at the 3' end.

Example 2

Construction of *Arabidopsis* Recombinant Expression Vectors and the Transfection of *Agrobacterium* with the Recombinant Expression Vectors 1. Construction of the *Arabidopsis* Recombinant Cloning Vector DBN01-T Containing 24DT07 Nucleotide Sequence The synthesized 24DT07 nucleotide sequence was subcloned into cloning vector pGEM-T (Promega, Madison, USA, CAT: A3600), to get recombinant cloning vector DBN01-T following the instructions of Promega pGEM-T vector, and the construction process was shown in FIG. 1 (wherein the Amp is ampicillin resistance gene; f1 is the replication origin of phage f1; LacZ is initiation codon of LacZ; SP6 is the promoter of SP6 RNA polymerase; T7 is the promoter of T7 RNA polymerase; 24DT07 is 24DT07 nucleotide sequence (SEQ ID NO: 1); MCS is multiple cloning sites).

The recombinant cloning vector DBN01-T was then transformed into *E. coli* T1 competent cell (Transgen, Beijing, China, the CAT: CD501) through heat shock method. The heat shock conditions were as follows: 50 µl of *E. coli* T1 competent cell and 10 µl of plasmid DNA (recombinant cloning vector DBN01-T) were incubated in water bath at 42° C. for 30 seconds. Then the *E. coli* cells were incubated in water bath at 37° C. for 1 h (100 rpm in a shaking incubator) and then were grown on a LB plate (10 g/L Tryptone, 5 g/L yeast extract, 10 g/L NaCl, 15 g/L Agar and pH was adjusted to 7.5 with NaOH) coated on the surface with IPTG (Isopropyl thio-beta-D-galactose glucoside), X-gal (5-bromine-4-chlorine-3-indole-beta-D-galactose glucoside) and ampicillin (100 mg/L) overnight. The white colonies were picked out and cultivated in LB broth (10 g/L Tryptone, 5 g/L yeast extract, 10 g/L NaCl, 100 mg/L ampicillin and pH was adjusted to 7.5 with NaOH) at 37° C. overnight. The plasmids thereof were extracted using alkaline lysis method as follows: the bacterial liquid was centrifuged for 1 min at 12000 rpm, the supernatant was discarded and the pellet was resuspended in 100 µl of ice-chilled solution I (25 mM Tris-HCl, 10 mM EDTA (ethylenediaminetetraacetic acid) and 50 mM glucose, pH=8.0); then 150 µl of freshly prepared solution II (0.2 M NaOH, 1% SDS (sodium dodecyl sulfate)) was added and the tube was reversed 4 times, mixed and then put on ice for 3-5 minutes; 150 µl of cold solution III (4 M potassium acetate and 2 M acetic acid) was added, thoroughly mixed immediately and incubated on ice for 5-10 minutes; the mixture was centrifuged at 12000 rpm at 4° C. for 5 minutes, two volumes of anhydrous ethanol were added into the supernatant, mixed and then placed at room temperature for 5 minutes; the mixture was centrifuged at 12000 rpm at 4° C. for 5 minutes, the supernatant was discarded and the pellet was dried after washed with 70% ethanol (V/V); 30 µl TE (10 mM Tris-HCl, 1 mM EDTA, pH=8.0) containing RNase (20 µg/ml) was added to dissolve the precipitate; the mixture was incubated at 37° C. in a water bath for 30 min to digest RNA and stored at −20° C. for the future use.

After the extracted plasmids were confirmed with restriction enzymes SpeI and KasI, the positive clones were verified through sequencing. The results showed that said 24DT07 nucleotide sequence inserted into the recombinant cloning vector DBN01-T was the sequence set forth in SEQ ID NO: 1 in the sequence listing, indicating that 24DT07 nucleotide sequence was correctly inserted.

The synthesized, substituted 24DT07 nucleotide sequence was inserted into cloning vector pGEM-T to get recombinant cloning vector DBN02-T following the process for constructing recombinant cloning vector DBN01-T as described above, wherein mi24DT07 was substituted 24DT07 nucleotide sequence (SEQ ID NO: 3). The substituted 24DT07 nucleotide sequence in the recombinant cloning vector DBN02-T was verified to be correctly inserted with restriction enzyme digestion and sequencing.

The synthesized, truncated 24DT07 nucleotide sequence was inserted into cloning vector pGEM-T to get recombinant cloning vector DBN03-T following the process for constructing cloning vector DBN01-T as described above, wherein mt24DT07 was truncated 24DT07 nucleotide sequence (SEQ ID NO: 4). The truncated 24DT07 nucleotide sequence in the recombinant cloning vector DBN03-T was verified to be correctly inserted with restriction enzyme digestion and sequencing.

The synthesized, added 24DT07 nucleotide sequence was inserted into cloning vector pGEM-T to get recombinant cloning vector DBN04-T following the process for constructing cloning vector DBN01-T as described above, wherein ma24DT07 was added 24DT07 nucleotide sequence (SEQ ID NO: 5). The added 24DT07 nucleotide sequence in the recombinant cloning vector DBN04-T was verified to be correctly inserted with restriction enzyme digestion and sequencing.

Figure 2:
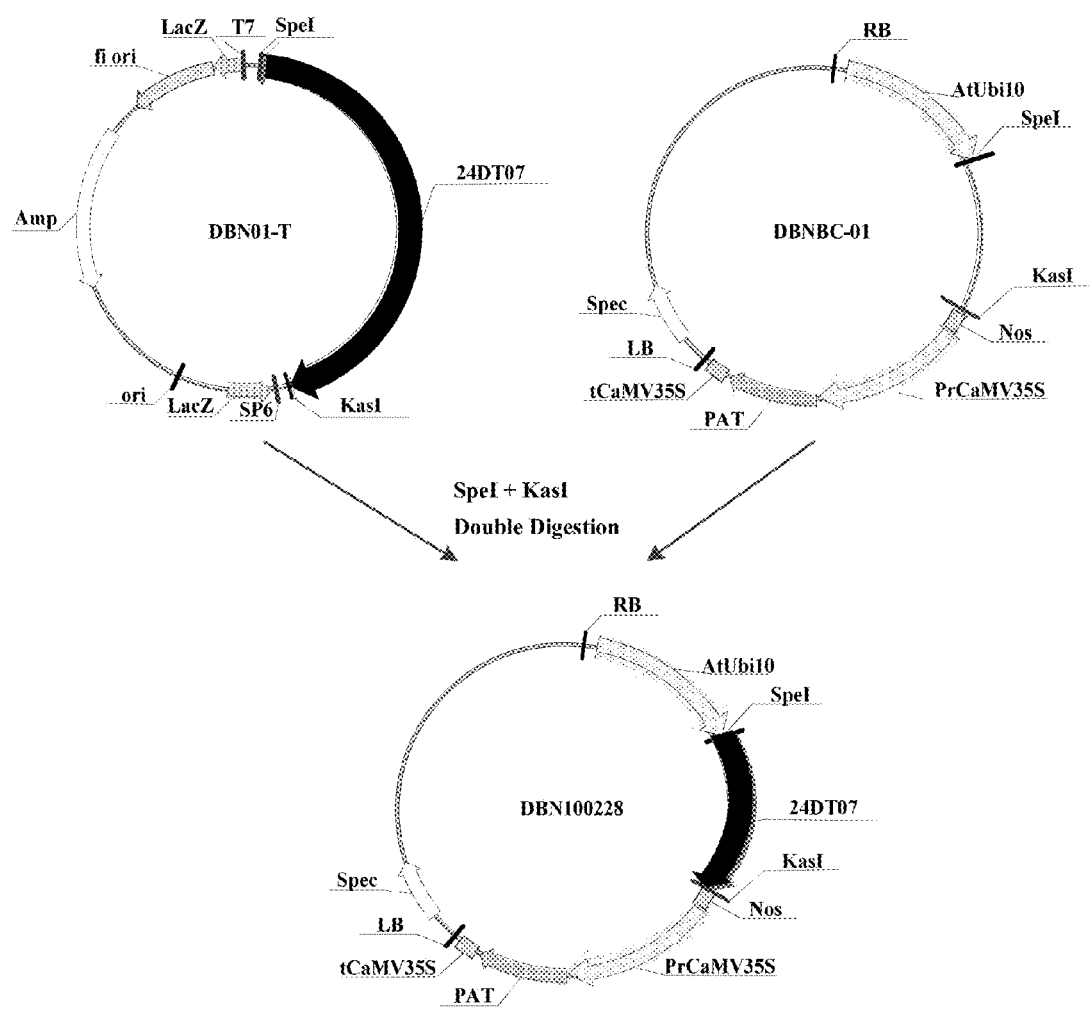
FIG. 2 shows the scheme to construct the recombinant expression vector DBN100228 containing 24DT07 nucleotide sequence.

2. Construction of the *Arabidopsis* Recombinant Expression Vector DBN100228 Containing 24DT07 Nucleotide Sequence The recombinant cloning vector DBN01-T and expression vector DBNBC-01 (Vector backbone: pCAMBIA2301, available from CAMBIA institution) were digested with restriction enzymes SpeI and KasI. The cleaved 24DT07 nucleotide sequence fragment was ligated between the restriction sites SpeI and KasI of the expression vector DBNBC-01 to construct the recombinant expression vector DBN100228. The construction scheme was shown in FIG. 2 (Spec: spectinomycin gene; RB: right border; AtUbi10: *Arabidopsis* Ubiquitin (Ubiquitin) 10 gene promoter (SEQ ID NO: 6); 24DT07: 24DT07 nucleotide sequence (SEQ ID NO: 1); Nos: terminator of nopaline synthetase gene (SEQ ID NO: 7); prCaMV35S: Cauliflower mosaic virus 35S promoter (SEQ ID NO:8); PAT: glufosinate acetyl transferase gene (SEQ ID NO:9); tCaMV35S: Cauliflower mosaic virus 35S terminator (SEQ ID NO: 10); LB: left border).

The recombinant expression vector DBN100228 was transformed into *E. coli* T1 competent cells with heat shock method as follows: 50 μl of *E. coli* T1 competent cell and 10 μl of plasmid DNA (recombinant expression vector DBN100228) were incubated in water bath at 42° C. for 30 seconds. Then the *E. coli* cells were incubated in water bath at 37° C. for 1 hour (100 rpm in a shaking incubator) and then were grown on a LB solid plate (10 g/L Tryptone, 5 g/L yeast extract, 10 g/L NaCl, 15 g/L Agar and pH was adjusted to 7.5 with NaOH) containing 50 mg/L spectinomycin at 37° C. for 12 hours. The white colonies were picked out and cultivated in LB broth (10 g/L Tryptone, 5 g/L yeast extract, 10 g/L NaCl, 50 mg/L spectinomycin and pH was adjusted to 7.5 with NaOH) at 37° C. overnight. The plasmids thereof were extracted using alkaline lysis method. After the extracted plasmids were confirmed with restriction enzymes SpeI and KasI, the positive clones were verified through sequencing. The results showed that the nucleotide sequence between restriction sites SpeI and KasI in the recombinant expression vector DBN100228 was the nucleotide sequence set forth in SEQ ID NO: 1 in the sequence listing, i.e. 24DT07 nucleotide sequence.

Following the process for constructing recombinant expression vector DBN100228 as described above, recombinant cloning vector DBN02-T was digested with restriction enzymes SpeI and KasI to cleave the substituted 24DT07 nucleotide sequence which then was inserted into the expression vector DBNBC-01 to get the recombinant expression vector DBN100228-i. Restriction enzyme digestion and sequencing verified that the nucleotide sequence between restriction sites SpeI and KasI in the recombinant expression vector DBN100228-i was the substituted 24DT07 nucleotide sequence.

Following the process for constructing recombinant expression vector DBN100228 as described above, recombinant cloning vector DBN03-T was digested with restriction enzymes SpeI and KasI to cleave the truncated 24DT07 nucleotide sequence which then was inserted into the expression vector DBNBC-01 to get the recombinant expression vector DBN100228-t. Restriction enzyme digestion and sequencing verified that the nucleotide sequence between restriction sites SpeI and KasI in the recombinant expression vector DBN100228-t was the truncated 24DT07 nucleotide sequence.

Following the process for constructing recombinant expression vector DBN100228 as described above, recombinant cloning vector DBN04-T was digested with restriction enzymes SpeI and KasI to cleave the added 24DT07 nucleotide sequence which then was inserted into the expression vector DBNBC-01 to get the recombinant expression vector DBN100228-a. Restriction enzyme digestion and sequencing verified that that the nucleotide sequence between restriction sites SpeI and KasI in the recombinant expression vector DBN100228-a was the added 24DT07 nucleotide sequence.

3. Construction of the *Arabidopsis* Recombinant Expression Vector DBN100228N Containing Control Sequence Following the process for constructing recombinant cloning vector DBN01-T comprising 24DT07 nucleotide sequence as described in part 1 of Example 2, recombinant cloning vector DBN01R-T containing control sequence was constructed by using control sequence (SEQ ID NO: 11). The positive clones were verified through sequencing. The results showed that the natural nucleotide sequence inserted into the recombinant cloning vector DBN01R-T was the sequence set forth in SEQ ID NO: 11 in the sequence listing, indicating that control nucleotide sequence was correctly inserted.

Figure 3:
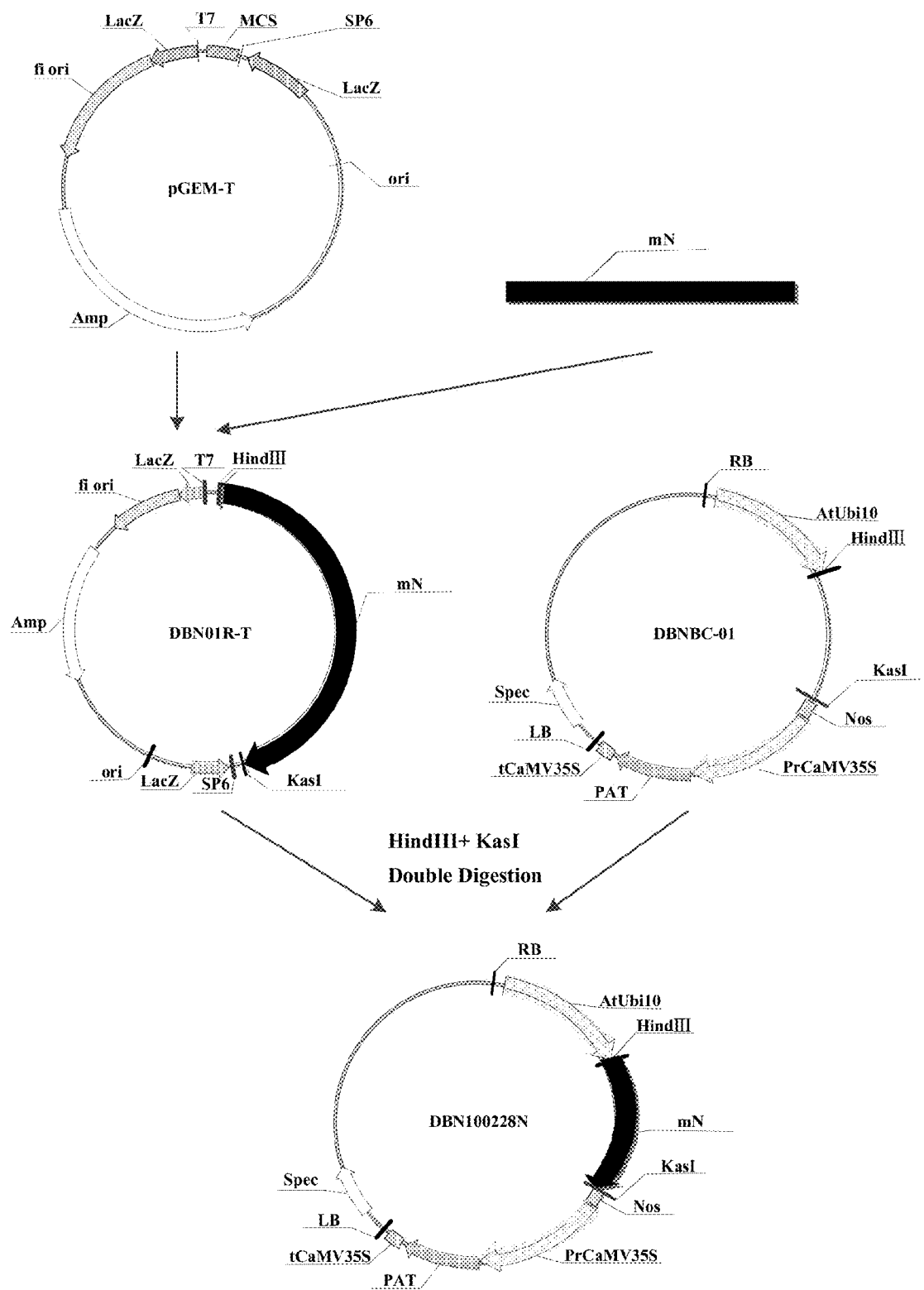
FIG. 3 shows the scheme to construct the recombinant expression vector DBN100228N containing control sequence.

Following the process for constructing recombinant expression vector DBN100228 containing 24DT07 nucleotide sequence as described in part 2 of Example 2, recombinant expression vector DBN100228N containing natural sequence was constructed using the natural sequence and the construction process was shown in FIG. 3 ((Vector backbone: pCAMBIA2301, available from CAMBIA institution); Spec: spectinomycin gene; RB: right border; AtUbi10: *Arabidopsis* Ubiquitin (Ubiquitin) 10 gene promoter (SEQ ID NO: 6); mN: control sequence (SEQ ID NO: 11); Nos, terminator of nopaline synthetase gene (SEQ ID NO: 7); prCaMV35S: Cauliflower mosaic virus 35S promoter (SEQ ID NO:8); PAT: glufosynat acetyl transferase gene (SEQ ID NO:9); tCaMV35S: Cauliflower mosaic virus 35S terminator (SEQ ID NO: 10); LB: left border). The positive clones were verified through sequencing. The results showed that the control sequence inserted into the recombinant expression vector DBN100228N was the sequence set forth in SEQ ID NO: 11 in the sequence listing, indicating that control sequence was correctly inserted.

4. Transfection of *Agrobacterium tumefaciens* with the *Arabidopsis* Recombinant Expression Vectors The correctly constructed recombinant expression vectors DBN100228, DBN100228-i, DBN100228-t, DBN100228-a and DBN100228N (control sequence) were transfected into *Agrobacterium* GV3101 following liquid nitrogen rapid-freezing method as follows: 100 mL *Agrobacterium* GV3101 and 3 mL plasmid DNA (recombinant expression vector) were put into liquid nitrogen for 10 minutes and then incubated in water bath at 37° C. for 10 minutes. Then the transfected *Agrobacterium* GV3101 cells were inoculated in LB broth and cultivated at 28° C., 200 rpm for 2 hours and spreaded on a LB plate containing 50 mg/L of rifampicin (Rifampicin) and 100 mg/L of spectinomycin until positive mono colonies appeared. The positive mono colonies were picked up and cultivated and the plasmids thereof were extracted. Recombinant expression vectors DBN100228, DBN100228-i, DBN100228-t, and DBN100228-a DBN100228N (control sequence) were verified with restriction enzymes StyI and BglII and recombinant expression vector DBN100228N (control sequence) was verified with restriction enzymes StyI and BglI. The results showed that the recombinant expression vectors DBN100228, DBN100228-i, DBN100228-t, DBN100228-a and DBN100228N (natural sequence) were correct in structure, respectively.

Example 3

Obtaining of the *Arabidopsis* Plant with Inserted 24DT07 Nucleotide Sequence The wild-type *Arabidopsis* seeds were suspended in 0.1% agarose solution and kept at 4° C. for 2 days so as to meet the need for dormancy to ensure the synchronous germination of seeds. Vermiculite and horses dung were mixed together and irrigated wet with water underground. The soil mixture was dewatered for 24 hours. The pretreated seeds were cultivated in the soil mixture and covered with a moisturizing mask for 7 days. The seeds were germinated and the plants were cultivated in a greenhouse at a constant temperature of 22° C. with constant moisture of 40-50% and a long day condition with the light intensity of 120-150 µmol/m² s (16 hours of light/8 hours of darkness). The plants were irrigated with Hoagland nutrient solution at first and then with deionized water to keep the soil moist but not drenched.

Floral dip method was used to transform *Arabidopsis*. One or more YEP media containing 100 mg/L of spectinomycin and 10 mg/L of rifampicin of 15-30 ml were inoculated with the selected *Agrobacterium* colonies as a preculture. The preculture was incubated at 28° C. and 220 rpm overnight. Each preculture was used to inoculate two cultures of 500 ml YEP media containing spectinomycin (100 mg/L) and rifampicin (10 mg/L) and the cultures were incubated at 28° C. in a shaking incubator overnight. Cultures were centrifuged at 8700×g for 10 minutes at room temperature to precipitate cells and the obtained supernatant was discarded. The cell pellets were gently resuspended in 500 ml of permeable medium which contains ½×MS salts/vitamin B5, 10% (w/v) sucrose, 0.044 µM Benzylaminopurine (10 µl/L (1 mg/ml stock solution in DMSO)) and 300 µl/L Silvet L-77. About 1 month old plants were soaked in the medium for 15 seconds and the latest inflorescences were ensured to be submerged. Then plants were put down by side and covered (transparent or non-transparent) for 24 hours, then washed with water and placed vertically. The plants were cultivated at 22° C. in a light cycle of 16 hours of light/8 hours of darkness. Seeds were harvested after soaked for 4 weeks.

The newly harvested $T_1$ seeds (24DT07 nucleotide sequence, 24DT07 substituted nucleotide sequence, 24DT07 truncated nucleotide sequences, 24DT07 added nucleotide sequence and natural sequence) were dried at room temperature for 7 days. The seeds were cultivated in germination plates (26.5×51 cm), 200 mg $T_1$ seeds (about 10000 seeds)/plate. The seeds have already been suspended in 40 ml of 0.1% agarose solution and stored at 4° C. for 2 days to meet the need for dormancy to ensure the synchronous germination of seeds.

Vermiculite and horses dung were mixed together and irrigated wet with water underground and drained through gravity. The pretreated seeds (40 ml each one) were uniformly planted on the soil mixture by using pipette and covered with moisturizing mask for 4 to 5 days. The mask was removed 1 day before the initial transformant selection by spraying glufosinate-ammonium (selection of the co-transformed PAT gene) after germination.

On 7 days after planting (DAP) and 11 DAP respectively, the T1 plants (cotyledon stage and 2-4 leaves stage, respectively) were sprayed with 0.2% of Liberty herbicide solution (200 g ai/L glufosinate-ammonium) using DeVilbiss compressed air nozzle at a spraying volume of 10 ml/disc (703 L/ha) so as to provide effective amount of glufosinate-ammonium (280 g ai/ha) for each application. The survival plants (actively growing plants) were verified 4 to 7 days after the last spraying and transferred into the square pot (7 cm×7 cm) made from vermiculite and horses dung (3-5 plants per pot). The transplanted plants were covered with moisturizing mask for 3-4 days and placed in culture room at 22° C. or directly into the greenhouse as described above. Then the mask was removed and the plants were planted in greenhouse (22±5° C., 50±30% RH, 14 hours of lighting: 10 hours of darkness, minimum 500 µE/m² s¹ natural light+ complement light) at least one day before testing the ability of 24DT07 to provide the resistance to phenoxy auxin herbicide.

Example 4

Herbicide Resistance Effect Test of the Transgenic *Arabidopsis*

24DT07 gene was used to transform *Arabidopsis* for the first time. At first, $T_1$ transformants were selected from the background of un-transformed seeds, using glufosinate-ammonium selection scheme. About 40000 $T_1$ seeds are screened among which 195 strains of T1 generation positive transformants (PAT gene) were identified, i.e. the transformation efficiency was about 0.5%. Herbicide resistance effect tests to 2,4-D dimethyl ammonium salt and agroxone of *Arabidopsis* $T_1$ plants transformed with 24DT07 nucleotide sequence, substituted 24DT07 nucleotide sequence, truncated 24DT07 nucleotide sequence, added 24DT07 nucleotide sequence, control nucleotide sequence respectively and wild-type *Arabidopsis* plants were performed after 18 days of planting.

Figure 4:
FIG. 4 shows the herbicide-resistant effect of the transgenic Arabidopsis $T_1$ plant.
Figure 4:
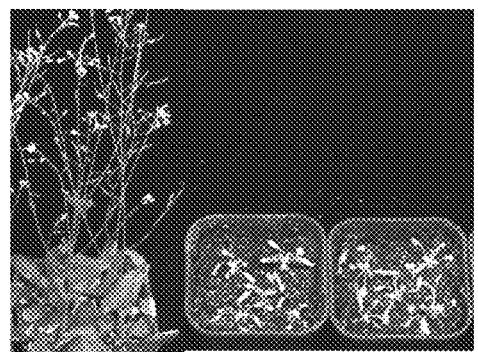
Figure 4:
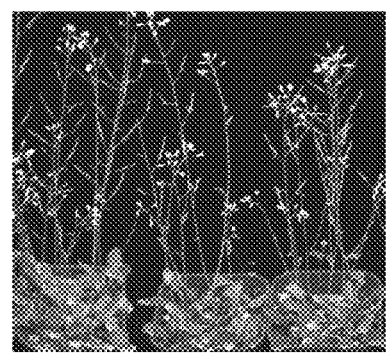

*Arabidopsis* $T_1$ plants transformed with 24DT07 nucleotide sequence, substituted 24DT07 nucleotide sequence, truncated 24DT07 nucleotide sequence, added 24DT07 nucleotide sequence and control nucleotide sequence respectively and wild-type *Arabidopsis* plants were sprayed with 2,4-D dimethyl ammonium salt (560 g ae/ha, 1-fold concentration in field), agroxone (560 g ae/ha, 1-fold concentration in field) and blank solvent (water). Resistance conditions of the plants were counted 7 days and 14 days after spraying. Plants with growth conditions consistent with blank solvent (water) 7 days after spaying were classified as highly resistant plants; Plants with curly rosette leaves 7 days after spaying were classified as moderately resistant plants; Plants incapable of bolting 14 days after spaying were classified as low-resistant plants and the dead plants 14 days after spaying were classified as non-resistant plants. Because each *Arabidopsis* $T_1$ plant is an independent transformation event, significant differences of individual $T_1$ responses can be expected under a given dose. The results were shown in Table 1 and FIG. 4.

TABLE 1

Herbicide resistance results of transgenic *Arabidopsis* $T_1$ plants

| Treatment | *Arabidopsis* genotype | Highly resistant | Moderately resistant | Lowly resistant | Non-resistant | Sum |
|---|---|---|---|---|---|---|
| Blank solvent (H₂O) | 24DT07 | 19 | 0 | 0 | 0 | 19 |
| | 24DT07-i | 17 | 0 | 0 | 0 | 17 |
| | 24DT07-t | 20 | 0 | 0 | 0 | 20 |
| | 24DT07-a | 18 | 0 | 0 | 0 | 18 |
| | Control | 20 | 0 | 0 | 0 | 20 |
| | Wild | 31 | 0 | 0 | 0 | 31 |

TABLE 1-continued

Herbicide resistance results of transgenic *Arabidopsis* T₁ plants

| Treatment | *Arabidopsis* genotype | Highly resistant | Moderately resistant | Lowly resistant | Non-resistant | Sum |
|---|---|---|---|---|---|---|
| 560 g ae/ha | 24DT07 | 20 | 4 | 0 | 0 | 24 |
| 2,4-D | 24DT07-i | 18 | 3 | 1 | 0 | 22 |
| dimethyl | 24DT07-t | 16 | 3 | 0 | 0 | 19 |
| ammonium | 24DT07-a | 17 | 5 | 0 | 0 | 22 |
| (1x 2,4-D) | Control | 0 | 0 | 0 | 18 | 18 |
|  | Wild | 0 | 0 | 0 | 20 | 20 |
| 560 g ae/ha | 24DT07 | 19 | 3 | 1 | 0 | 23 |
| agroxone | 24DT07-i | 17 | 4 | 1 | 0 | 22 |
| (1xMCPA) | 24DT07-t | 18 | 4 | 0 | 0 | 22 |
|  | 24DT07-a | 15 | 5 | 1 | 0 | 21 |
|  | Control | 0 | 0 | 0 | 17 | 17 |
|  | Wild | 0 | 0 | 0 | 16 | 16 |

For *Arabidopsis*, 50 g ae/ha of 2,4-D and agroxone is the effective dose to distinguish the sensitive plants from plants with average resistance. Results shown in Table 1 and FIG. 4 indicated that the 24DT07 gene confers herbicide resistance to individual *Arabidopsis* plants (only parts of the plants have the resistance because insertion sites of T1 generation plants are random. Therefore the resistance gene expression levels are different, resulting in the different levels of resistance), especially the phenoxy auxin herbicides. The wild-type *Arabidopsis* plants and *Arabidopsis* plants transformed with control sequence had no resistance to phenoxy auxin herbicide. In addition, resistance levels to 2,4-D dimethyl ammonium salt and agroxone of *Arabidopsis* T₁ plants transformed with 24DT07 nucleotide sequence, substituted 24DT07 nucleotide sequence, truncated 24DT07 nucleotide sequence and added 24DT07 nucleotide sequence didn't show significant differences.

Example 5

Figure 5:
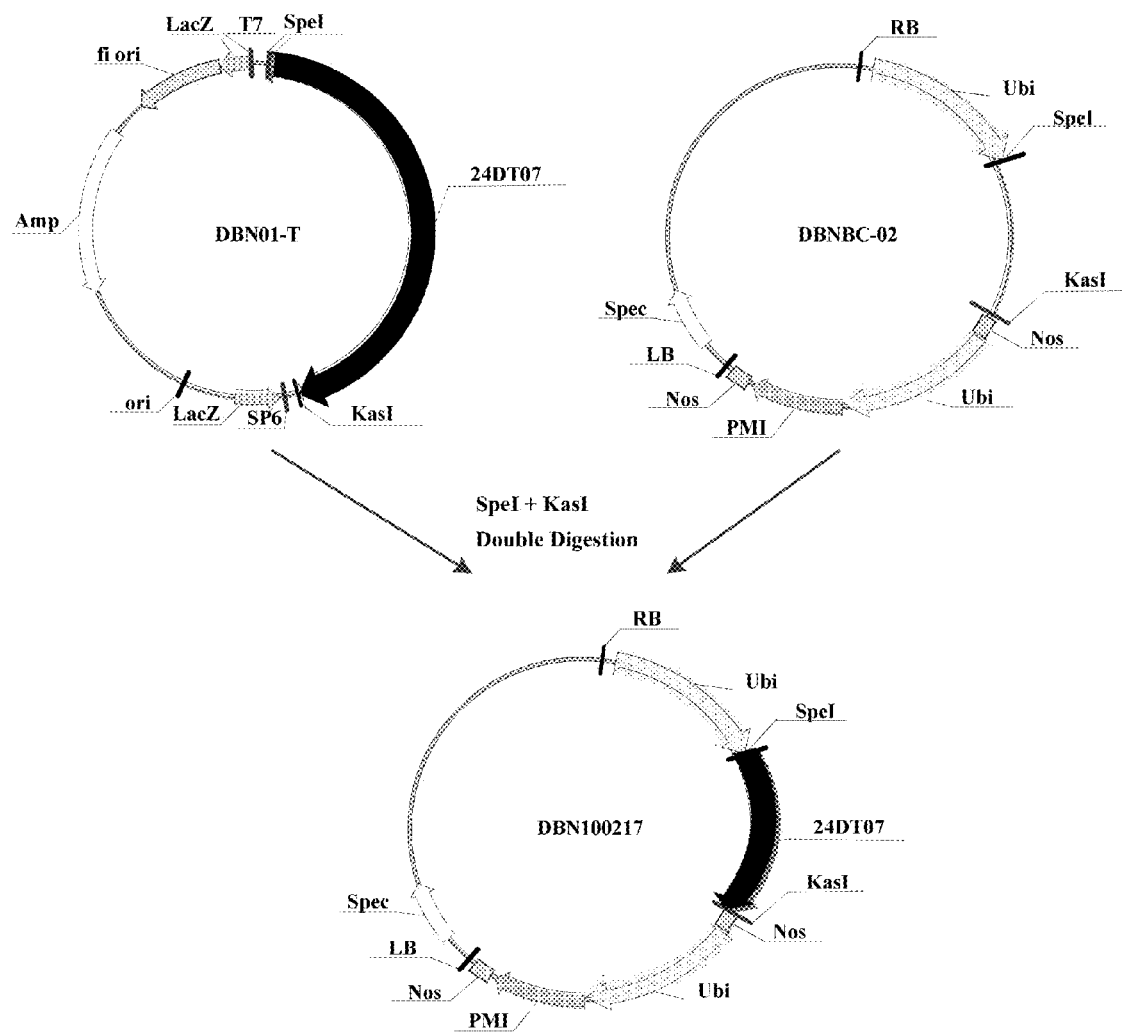
FIG. 5 shows the scheme to construct the recombinant expression vector DBN100217 containing 24DT07 nucleotide sequence.

Construction of the Corn Recombinant Expression Vector and Transfection of *Agrobacterium* with Recombinant Expression Vector 1. Construction of the Corn Recombinant Expression Vector DBN100217 Containing 24DT07 Nucleotide Sequence The recombinant cloning vector DBN01-T and expression vector DBNBC-02 (Vector backbone: pCAMBIA2301, available from CAMBIA institution) were digested with restriction enzymes SpeI and KasI. The cleaved 24DT07 nucleotide sequence fragment was ligated between the restriction sites SpeI and KasI of the expression vector DBNBC-01 to construct the recombinant expression vector DBN100217. SpeI and KasI restriction sites in the expression vector DBNBC-01 were also introduced using conventional enzyme digestion method. The construction scheme was shown in FIG. 5 (Spec: spectinomycin gene; RB: right border; Ubi: maize Ubiquitin (Ubiquitin) 1 gene promoter (SEQ ID NO: 12); 24DT07: 24DT07 nucleotide sequence (SEQ ID NO: 1); Nos: terminator of nopaline synthetase gene (SEQ ID NO: 7); PMI: phosphomannose isomerase gene (SEQ ID NO: 13); LB: left border).

The recombinant expression vector DBN100217 was transformed into *E. coli* T1 competent cells with heat shock method as follows: 50 μl of *E. coli* T1 competent cell and 10 μl of plasmid DNA (recombinant expression vector DBN100217) were incubated in water bath at 42° C. for 30 seconds. Then the *E. coli* cells were incubated in water bath at 37° C. for 1 hour (100 rpm in a shaking incubator) and then were grown on a LB solid plate (10 g/L Tryptone, 5 g/L yeast extract, 10 g/L NaCl, 15 g/L Agar and pH was adjusted to 7.5 with NaOH) containing 50 mg/L spectinomycin (Spectinomycin) at 37° C. for 12 hours. The white colonies were picked out and cultivated in LB broth (10 g/L Tryptone, 5 g/L yeast extract, 10 g/L NaCl, 50 mg/L spectinomycin and pH was adjusted to 7.5 with NaOH) at 37° C. overnight. The plasmids thereof were extracted using alkaline lysis method. After the extracted plasmids were confirmed with restriction enzymes SpeI and KasI, the positive clones were verified through sequencing. The results showed that the nucleotide sequence between restriction sites SpeI and KasI in the recombinant expression vector DBN100217 was the nucleotide sequence set forth in SEQ ID NO: 1 in the sequence listing, i.e. 24DT07 nucleotide sequence.

Following the process for constructing recombinant expression vector DBN100217 as described above, recombinant cloning vector DBN02-T were digested with restriction enzymes SpeI and KasI to cleave the substituted 24DT07 nucleotide sequence which then was inserted into the expression vector DBNBC-01 to get the recombinant expression vector DBN100217-i. Restriction enzyme digestion and sequencing verified that the nucleotide sequence between restriction sites SpeI and KasI in the recombinant expression vector DBN100217-i was the substituted 24DT07 nucleotide sequence.

Following the process for constructing recombinant expression vector DBN100217 as described above, recombinant cloning vector DBN03-T were digested with restriction enzymes SpeI and KasI to cleave the truncated 24DT07 nucleotide sequence which then was inserted into the expression vector DBNBC-01 to get the recombinant expression vector DBN100217-t. Restriction enzyme digestion and sequencing verified that the nucleotide sequence between restriction sites SpeI and KasI in the recombinant expression vector DBN100217-t was the truncated 24DT07 nucleotide sequence.

Following the process for constructing recombinant expression vector DBN100217 as described above, recombinant cloning vector DBN04-T were digested with restriction enzymes SpeI and KasI to cleave the added 24DT07 nucleotide sequence which then was inserted into the expression vector DBNBC-01 to get the recombinant expression vector DBN100217-a. Restriction enzyme digestion and sequencing verified that the nucleotide sequence between restriction sites SpeI and KasI in the recombinant expression vector DBN100217-a was the added 24DT07 nucleotide sequence.

2. Construction of the Corn Recombinant Expression Vector DBN100217N Containing Control Nucleotide Sequence Following the process for constructing recombinant cloning vector DBN01-T containing 24DT07 nucleotide sequences described in part 1 of Example 2, recombinant cloning vector DBN01R-T containing control sequence was constructed by using control sequence (SEQ ID NO: 11). The positive clones were verified through sequencing. The results showed that the natural nucleotide sequence inserted into the recombinant cloning vector DBN01R-T was the sequence set forth in SEQ ID NO: 11 in the sequence listing, indicating that control nucleotide sequence was correctly inserted.

Figure 6:
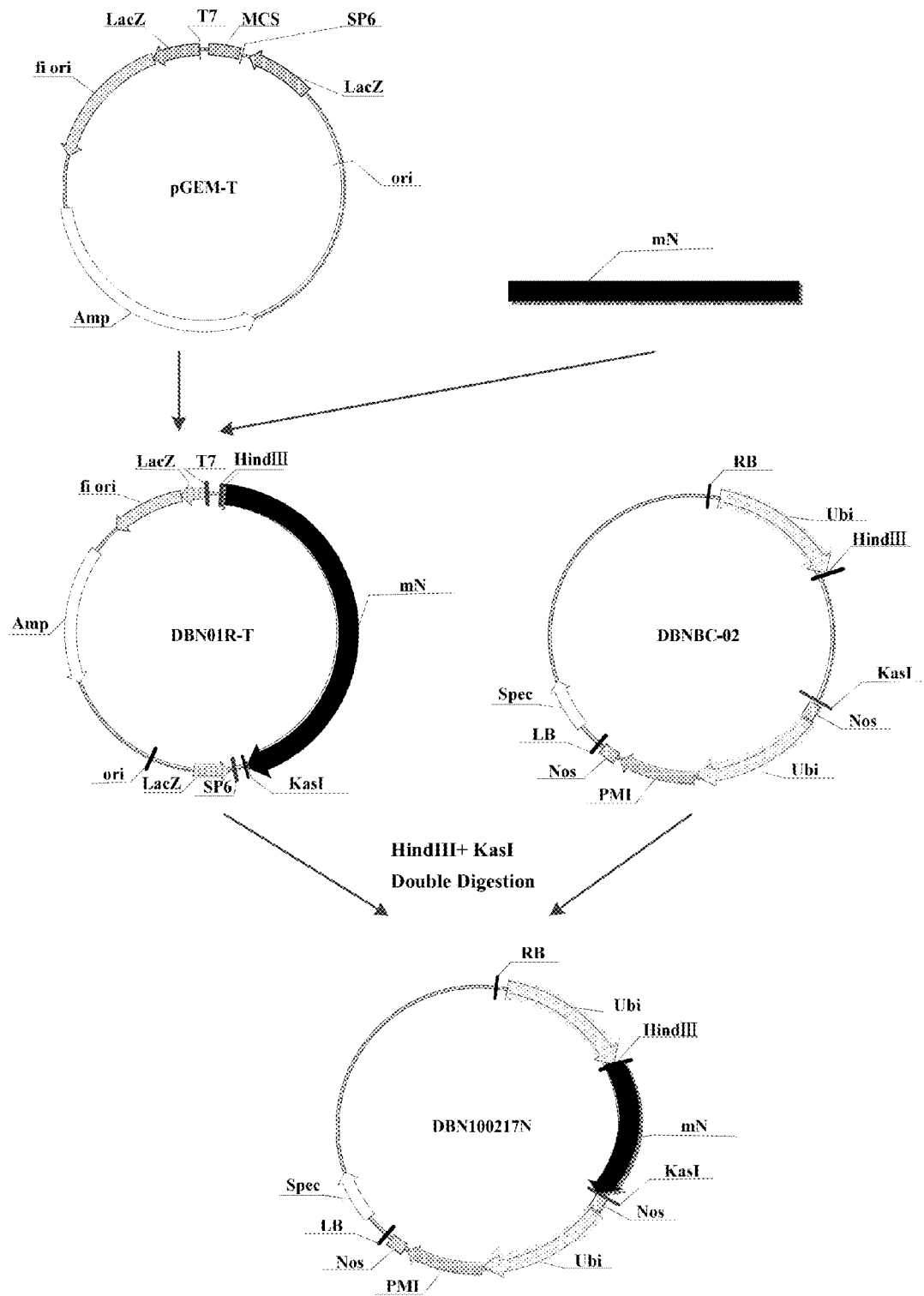
FIG. 6 shows the scheme to construct the recombinant expression vector DBN100217N containing control sequence.

Following the process for constructing recombinant expression vector DBN100217 containing 24DT07 nucleotide sequence as described in part 1 of Example 5, recombinant expression vector DBN100217N containing natural sequence was constructed by using the natural sequence and the construction process was shown in FIG. 6 (Vector backbone: pCAMBIA2301, available from CAMBIA institution); Spec: spectinomycin gene; RB: right border; ZmUbi1:maize Ubiquitin (ubiquitin) 1 gene promoter (SEQ ID NO: 12); mN: control sequence (SEQ ID NO: 11); Nos: terminator of nopaline synthetase gene (SEQ ID NO: 7); PMI: phosphomannose-isomerase gene (SEQ ID NO: 13); LB: left border). The positive clones were verified through sequencing. The results showed that the control sequence inserted into the recombinant expression vector DBN100228N was the sequence set forth in SEQ ID NO: 11 in the sequence listing, indicating that the control nucleotide sequence was correctly inserted.

3. Transfection of *Agrobacterium tumefaciens* with Corn Recombinant Expression Vectors The correctly constructed recombinant expression vectors DBN100217, DBN100217-i, DBN100217-t, DBN100217-a and DBN100217N (control sequence) were transfected into *Agrobacterium* LBA4404 (Invitrogen, Chicago, USA, Cat. No: 18313-015) following liquid nitrogen rapid-freezing method as follows: 100 μL *Agrobacterium* LBA4404 and 3 μL plasmid DNA (recombinant expression vector) were put into liquid nitrogen and kept for 10 minutes and then incubated in water bath at 37° C. for 10 minutes. Then the transfected *Agrobacterium* LBA4404 cells were inoculated in LB tube and cultivated at 28° C., 200 rpm for 2 hours and spreaded on a LB plate containing 50 mg/L of rifampicin (Rifampicin) and 100 mg/L of spectinomycin until positive mono colonies appeared. The positive mono colonies were picked up and cultivated and the plasmids thereof were extracted. Recombinant expression vectors DBN100217, DBN100217-i, DBN100217-t and DBN100217-a were verified with restriction enzymes EcoRI and BglII and DBN100217N (control sequence) was verified with restriction enzymes StyI and BglI. The results showed that the recombinant expression vectors DBN100217, DBN100217-i, DBN100217-t, DBN100217-a and DBN100217N (natural sequence) were correct in structures, respectively.

Example 6

Obtaining and Verification of the Transgenic Corn Plants with Inserted 24DT07 Nucleotide Sequence According to the conventional *Agrobacterium* transfection method, the maize cultivar Zong 31 (Z31) was cultivated in sterilized conditions and the young embryo was co-cultivated with the *Agrobacterium* strains constructed in part 3 of Example 5 so as to introduce T-DNAs in the recombinant expression vectors DBN100217, DBN100217-i, DBN100217-t, DBN100217-a and DBN100217N (natural sequence) constructed in part 1 and 2 of Example 5 (including corn Ubiquitin 1 gene promoter sequence, 24DT07 nucleotide sequence, 24DT07 substituted nucleotide sequence, 24DT07 truncated nucleotide sequence, 24DT07 added nucleotide sequence, control nucleotide sequence, PMI gene and Nos terminator sequence) into the maize genome. Maize plants containing 24DT07 nucleotide sequence, 24DT07 substituted nucleotide sequence, 24DT07 truncated nucleotide sequence, 24DT07 added nucleotide sequence and control nucleotide sequence respectively were obtained and at the same time wild type corn plant was taken as a control.

As to the *Agrobacterium*-mediated transfection of maize, in brief, immature maize young embryo was isolated from corns and contacted with *Agrobacterium* suspension, in which the *Agrobacterium* can deliver the 24DT07 nucleotide sequence into at least one cell of one young embryo. (Step 1: infection step). In this step, optionally, young embryo was immersed in *Agrobacterium* suspension ($OD_{660}$=0.4~0.6, infection medium (4.3 g/L of MS salt, MS vitamins, 300 mg/L of casein, 68.5 g/L of sucrose, 36 g/L of glucose, 40 mg/L of Acetosyringone (AS), 1 mg/L of 2,4-dichlorophenoxyacetic acid (2,4-D), pH=5.3)) to initiate the inoculation. Young embryo and *Agrobacterium* were cocultivated for a period (3 days) (Step 2: cocultivation step). Optionally, the young embryo was cultivated on a solid medium (4.3 g/L of MS salt, MS vitamins, 300 mg/L of casein, 20 g/L of sucrose, 10 g/L of glucose, 100 mg/L of Acetosyringone (AS), 1 mg/L of 2,4-dichlorophenoxyacetic acid (2,4-D) and 8 g/L of Agar, pH=5.8) after the infection step. After this cocultivation step, a selective "recovery" step can be preceded. In the "recovery" step, the recovery medium (4.3 g/L of MS salt, MS vitamins, 300 mg/L of casein, 30 g/L of sucrose, 1 mg/L of 2,4-dichlorophenoxyacetic acid (2,4-D) and 8 g/L of Agar, pH=5.8) contains at least one kind of known *Agrobacterium*-inhibiting antibiotics (cephalosporin) without the selective agent for plant transfectants (Step 3: recovery step). Optionally, the young embryo was cultivated on a solid medium culture containing antibiotics but without selective agent so as to eliminate *Agrobacterium* and to provide a recovery period for the infected cells. Then, the inoculated young embryo was cultivated on a medium containing selective agent (mannose) and the transfected, growing callus was selected (Step 4: selection step). Optionally, the young embryo was cultivated on a selective solid medium containing selective agent (4.3 g/L of MS salt, MS vitamins, 300 mg/L of casein, 5 g/L of sucrose, 12.5 g/L of mannose, 1 mg/L of 2,4-dichlorophenoxyacetic acid (2,4-D) and 8 g/L of Agar, pH=5.8), resulting the selective growth of the transfected cells. Then, callus regenerated into plants (Step 5: regeneration step). Optionally, the callus was cultivated on a solid medium containing selective agent (MS differentiation medium and MS rooting medium) to regenerate into plants.

The obtained resistant callus was transferred to said MS differentiation medium (4.3 g/L MS salt, MS vitamins, 300 mg/L of casein, 30 g/L of sucrose, 2 mg/L of 6-benzyladenine, 5 g/L of mannose and 8 g/L of Agar, pH=5.8) and cultivated and differentiated at 25° C. The differentiated seedlings were transferred to said MS rooting medium (2.15 g/L of MS salt, MS vitamins, 300 mg/L of casein, 30 g/L of sucrose, 1 mg/L indole-3-acetic acid and 8 g/L of agar, pH=5.8) and cultivated to about 10 cm in height at 25° C. Next, the seedlings were transferred to and cultivated in the greenhouse until fructification. In the greenhouse, the maize plants were cultivated at 28° C. for 16 hours and at 20° C. for 8 hours every day.

2. Verification of Transgenic Corn Plants with Inserted 24DT07 Gene Using TaqMan Technique 100 mg of leaves from every transfected corn plant (corn plant transfected with 24DT07 nucleotide sequence, 24DT07 substituted nucleotide sequence, 24DT07 truncated nucleotide sequence, 24DT07 added nucleotide sequence or control nucleotide sequence, respectively) was taken as sample respectively. Genomic DNA thereof was extracted using DNeasy Plant Maxi Kit (Qiagen) and the copy number of 24DT07 gene was quantified through Taqman probe-based fluorescence quantitative PCR assay. Wild type maize plant was taken as a control and analyzed according to the processes as described above. Experiments were carried out in triplicate and the results were the mean values.

The specific method for detecting the copy number of 24DT07 gene was described as follows:

Step 11: 100 mg of leaves from every transfected corn plant (corn plant transfected with 24DT07 nucleotide sequence, 24DT07 substituted nucleotide sequence, 24DT07 truncated nucleotide sequence, 24DT07 added nucleotide sequence or control nucleotide sequence, respectively) and wild type corn plant was taken and grinded into homogenate in a mortar in liquid nitrogen respectively. It was in triplicate for each sample.

Step 12: the genomic DNAs of the samples above were extracted using DNeasy Plant Mini Kit (Qiagen) following the product instruction thereof.

Step 13: the genome DNA concentrations of the above samples were determined using NanoDrop 2000 (Thermo Scientific).

Step 14: the genome DNA concentrations were adjusted to the same range of 80-100 ng/μl.

Step 15: the copy numbers of the samples were quantified using Taqman probe-based fluorescence quantitative PCR assay, the quantified sample with known copy number was taken as a standard sample and the wild type maize plant was taken as a control. It was carried out in triplicate for every sample and the results were the mean values. Primers and the probes used in the fluorescence quantitative PCR were shown as below.

The following primers and probe were used to detect 24DT07 nucleotide sequence, 24DT07 substituted nucleotide sequence, 24DT07 truncated nucleotide sequence and 24DT07 added nucleotide sequence:

```
Primer 1:
CGCTATGAACAGATACGCAGTGC (as shown in
SEQ ID NO: 14 in the sequence listing);

Primer 2:
AAGCCTTGGCGAAGTCGATC (as shown in
SEQ ID NO: 15 in the sequence listing);

Probe 1:
TGCTGTCCTGTAAGTGGCTGTCCCCTC (as shown in
SEQ ID NO: 16 in the sequence listing);
```

The following primers and probe were used to detect control sequence:

```
Primer 3:
TGCGTATTCAATTCAACGACATG (as shown in
SEQ ID NO: 17 in the sequence listing);

Primer 4:
CTTGGTAGTTCTGGACTGCGAAC (as shown in
SEQ ID NO: 18 in the sequence listing);

Probe 2:
CAGCGCCTTGACCACAGCTATCCC (as shown in
SEQ ID NO: 19 in the sequence listing);
```

PCR reaction system was as follows:

| | |
|---|---|
| JumpStart ™ Taq ReadyMix ™ (Sigma) | 10 μl |
| 50x primer/probe mixture | 1 μl |
| Genomic DNA | 3 μl |
| Water (ddH₂O) | 6 μl |

Said 50x primer/probe mixture contained 45 μl of each primer (1 mM), 50 μl of probe (100 μM) and 860 μl of 1× TE buffer and was stored in an amber tube at 4° C.

PCR reaction conditions were provided as follows:

| Step | Temperature | Time |
|---|---|---|
| 21 | 95° C. | 5 min |
| 22 | 95° C. | 30 s |
| 23 | 60° C. | 1 min |
| 24 | back to step 22 and repeated 40 times | |

Data were analyzed using software SDS 2.3 (Applied Biosystems).

The experimental results showed that all the nucleotide sequences of 24DT07 nucleotide sequence, 24DT07 substituted nucleotide sequence, 24DT07 truncated nucleotide sequence, 24DT07 added nucleotide sequence and the natural nucleotide sequence have been integrated into the genomes of the detected corn plants, respectively. Furthermore, all corn plants transfected 24DT07 nucleotide sequence, 24DT07 substituted nucleotide sequence, 24DT07 truncated nucleotide sequence, 24DT07 added nucleotide sequence and the control nucleotide sequence respectively contained single copy of 24DT07 gene.

Example 7

Herbicide-Resistance Effect Tests of the Transgenic Corn Plants

Herbicide resistance effects tests to 2,4-D dimethyl ammonium salt and agroxone of maize plants containing 24DT07 nucleotide sequence, 24DT07 substituted nucleotide sequence, 24DT07 truncated nucleotide sequence, 24DT07 added nucleotide sequence, control nucleotide sequence respectively and wild type maize plants (stages V3-V4) were performed respectively.

Maize plants containing 24DT07 nucleotide sequence, 24DT07 substituted nucleotide sequence, 24DT07 truncated nucleotide sequence, 24DT07 added nucleotide sequence, control nucleotide sequence respectively and wild type maize plants were taken and spayed with 2,4-D dimethyl ammonium salt (8960 g ae/ha, 16-folds concentration in field), agroxone (8960 g ae/ha, 16-folds concentration in field) and blank solvent (water) respectively. Prop root development was counted 21 days after spaying. Three strains (S1, S2, and S3) of corn plants transfected with 24DT07 nucleotide sequence, two strains (S4 and S5) of corn plants transfected with 24DT07 substituted nucleotide sequence, two strains (S6 and S7) of corn plants transfected with 24DT07 truncated nucleotide sequence, two strains (S8 and S9) of corn plants transfected with 24DT07 added nucleotide sequence, two strains (S10 and S11) of corn plants transfected with control nucleotide sequence and 1 strain of wild type (CK) corn were selected and 10-15 plants from each stain were tested. The results were shown in Table 2.

TABLE 2

Results of herbicide-resistance effect tests of the transgenic corn T₁ plants

| Treatment | Corn genotype | Normal development of prop roots | Abnormal development of prop roots | Ratio of the normally developed prop roots |
|---|---|---|---|---|
| Blank solvent (water) | S1 | 13 | 0 | 100.00% |
| | S2 | 14 | 0 | 100.00% |
| | S3 | 12 | 0 | 100.00% |
| | S4 | 10 | 0 | 100.00% |
| | S5 | 12 | 0 | 100.00% |
| | S6 | 14 | 0 | 100.00% |
| | S7 | 14 | 0 | 100.00% |
| | S8 | 15 | 0 | 100.00% |
| | S9 | 11 | 0 | 100.00% |
| | S10 | 10 | 0 | 100.00% |
| | S11 | 11 | 0 | 100.00% |
| | CK | 16 | 0 | 100.00% |
| 8960 g ae/ha 2,4-D dimethyl ammonium salt (16x 2,4-D) | S1 | 13 | 2 | 86.67% |
| | S2 | 11 | 1 | 91.67% |
| | S3 | 12 | 0 | 100.00% |
| | S4 | 13 | 1 | 92.86% |
| | S5 | 12 | 0 | 100.00% |
| | S6 | 12 | 1 | 92.31% |
| | S7 | 14 | 1 | 93.33% |
| | S8 | 12 | 0 | 100.00% |
| | S9 | 13 | 0 | 100.00% |
| | S10 | 0 | 10 | 0% |
| | S11 | 0 | 11 | 0% |
| | CK | 0 | 16 | 0% |
| 8960 g ae/ha agroxone (16 x MCPA) | S1 | 14 | 1 | 93.33% |
| | S2 | 12 | 1 | 92.31% |
| | S3 | 13 | 0 | 100.00% |
| | S4 | 14 | 0 | 100.00% |
| | S5 | 13 | 1 | 92.86% |
| | S6 | 13 | 0 | 100.00% |
| | S7 | 11 | 1 | 91.67% |
| | S8 | 14 | 0 | 100.00% |
| | S9 | 13 | 0 | 100.00% |
| | S10 | 0 | 10 | 0% |
| | S11 | 0 | 10 | 0% |
| | CK | 0 | 16 | 0% |

Results in Table 2 indicated that the 24DT07 gene conferred high resistance against herbicides to the transgenic maize plants, especially the phenoxy auxin herbicides (since the monocotyledon plants inherently have certain resistance to phenoxy auxin herbicides, high levels of resistance appeared); while none of the wild type of corn plants and the corn plants transfected with control sequences showed high levels of resistance against herbicides. In addition, resistance levels against 2,4-D dimethyl ammonium salt and agroxone of corn plants transformed with 24DT07 nucleotide sequence, substituted 24DT07 nucleotide sequence, truncated 24DT07 nucleotide sequence and added 24DT07 nucleotide sequence didn't show significant differences.

Above all, both corn and *Arabidopsis thaliana* plants transfected with 24DT07 nucleotide sequence had high herbicide-resistance ability. Some codons of plant were employed in the herbicide-resistant gene 24DT07 in present application, resulting that the herbicide-resistant gene of present application is suitable to be expressed in plants. 24DT07 herbicide-resistant protein of present application has a broad herbicide-resistance spectrum, especially phenoxy auxin herbicides.

Finally what should be explained is that all the above examples are merely intentioned to illustrate the technical solutions of present application rather than to restrict present application. Although detailed description of this application has been provided by referring to the preferable examples, one skilled in the art should understand that the technical solutions of the application can be modified or equivalently substituted while still fall within the spirit and scope of the present application.

What is claimed is:

1. An herbicide-resistant protein selected from the group consisting of:
   (a) a protein encoded by nucleotide sequence set forth in SEQ ID NO: 3;
   (b) a protein encoded by nucleotide sequence set forth in SEQ ID NO: 4; and
   (c) a protein encoded by nucleotide sequence set forth in SEQ ID NO: 5.

2. An herbicide-resistant gene selected from the group consisting of:
   (a) a nucleotide sequence encoding the herbicide-resistant protein of claim 1; and
   (b) a nucleotide sequence completely complementary with a nucleotide sequence encoding the herbicide-resistant protein of claim 1.

3. A method for controlling weeds comprising a step of applying an effective amount of one or more herbicides to the field planted with plants comprising the herbicide-resistant gene of claim 2 or a nucleotide sequence encoding SEQ ID NO: 2.

4. A method for controlling weeds comprising a step of applying an effective amount of one or more herbicides to the field planted with plants comprising the herbicide-resistant gene of claim 2 or a nucleotide sequence encoding SEQ ID NO: 2, wherein the herbicide resistant gene of claim 2 or the nucleotide sequence encoding SEQ ID NO: 2 is produced from a transgenic host cell selected from the group consisting of plant cells, animal cells, bacteria, yeast, baculovirus, nematodes and algae.

5. The method for controlling weeds of claim 3, wherein the plant is selected from the group consisting of soybean, cotton, corn, rice, wheat, beet and sugarcane.

6. A method for controlling weeds comprising a step of applying an effective amount of one or more herbicides to the field planted with plants comprising the herbicide-resistant gene of claim 2 or a nucleotide sequence encoding SEQ ID NO: 2, wherein the herbicide resistant gene of claim 2 or the nucleotide sequence encoding SEQ ID NO: 2 is co-expressed in the plant with at least a second nucleotide sequence encoding a herbicide-resistant protein different from the herbicide-resistant gene of claim 2 and the nucleotide sequence encoding SEQ ID NO: 2.

7. The method for controlling weeds of claim 6, wherein said second nucleotide sequence encodes glyphosate-resistant protein, glufosinate ammonium resistant protein, 4-hydroxyphenylpyruvate dioxygenase, acetolactate synthase, cytochromes protein or protoporphyrinogen oxidase.

8. The method for controlling weeds of claim 3, wherein the herbicide is a phenoxy auxin.

9. The herbicide-resistant protein of claim 1, wherein the nucleotide sequence set forth in SEQ ID NO: 4 is part of a recombinant expression vector.

10. The herbicide-resistant protein of claim 1, wherein the nucleotide sequence set forth in SEQ ID NO: 4 is part of a recombinant expression vector and the recombinant expression vector comprises a nucleic acid sequence that is heterologous to SEQ ID NO: 4.

11. The herbicide-resistant protein of claim 1 selected from the group consisting of:
 (a) a protein encoded by nucleotide sequence set forth in SEQ ID NO: 3; and
 (b) a protein encoded by nucleotide sequence set forth in SEQ ID NO: 5.

12. A method for controlling weeds comprising a step of applying an effective amount of one or more herbicides to the field planted with plants comprising the herbicide-resistant gene of claim 2.

* * * * *